US012623011B2

(12) United States Patent
Crosbie et al.

(10) Patent No.: US 12,623,011 B2
(45) Date of Patent: May 12, 2026

(54) IMPLANTABLE PUMP FOR DIRECT SODIUM REMOVAL THERAPY HAVING ON-BOARD ANALYTE SENSOR

(71) Applicant: DSRCo BV, Ghent (BE)

(72) Inventors: Ian Crosbie, London (GB); Andreas Wirth, Simbach am Inn (DE); Oliver Goedje, Strasslach (DE)

(73) Assignee: DSRCo BV, Ghent (BE)

( * ) Notice: Subject to any disclaimer, the term of this patent is extended or adjusted under 35 U.S.C. 154(b) by 846 days.

(21) Appl. No.: 17/938,418

(22) Filed: Oct. 6, 2022

(65) Prior Publication Data

US 2023/0037921 A1 Feb. 9, 2023

Related U.S. Application Data

(63) Continuation of application No. 17/650,183, filed on Feb. 7, 2022, now Pat. No. 11,464,891, which is a
(Continued)

(51) Int. Cl.
*A61M 1/28* (2006.01)
*A61K 9/00* (2006.01)
(Continued)

(52) U.S. Cl.
CPC ............ *A61M 1/28* (2013.01); *A61K 9/0019* (2013.01); *A61K 9/08* (2013.01); *A61K 31/7004* (2013.01);
(Continued)

(58) Field of Classification Search
CPC ........ A61M 11/28; A61M 1/28; A61M 1/287; A61M 1/282; A61M 27/002;
(Continued)

(56) References Cited

U.S. PATENT DOCUMENTS

| | | |
|---|---|---|
| 3,233,610 A | 2/1966 | Charles et al. |
| 3,516,410 A | 6/1970 | Hakim et al. |
| (Continued) | | |

FOREIGN PATENT DOCUMENTS

| | | |
|---|---|---|
| CN | 101291634 A | 10/2008 |
| CN | 101485683 A | 7/2009 |
| (Continued) | | |

OTHER PUBLICATIONS

Clinical Pharmacology and Biopharmaceutics Review, Center for Drug Evaluation and Research, Approval Package for: Application No. 21-321, Aug. 31, 2001.
(Continued)

*Primary Examiner* — Lauren P Farrar
(74) *Attorney, Agent, or Firm* — Greenberg Traurig, LLP; Christopher C. Bolten; Robert D. Ward

(57) ABSTRACT

Systems and methods for performing Direct Sodium Removal (DSR) therapy are provided in which an implantable device includes a pump coupled to an inlet catheter designed for placement in a patient's peritoneal cavity, an outlet catheter designed to be coupled to the patient's bladder, and is operably coupled to an analyte sensor, the pump programmed to transfer and/or cease transfer of fluid from the patient's peritoneal cavity to the patient's bladder for voiding responsive to a level of analyte detected by the analyte sensor. In addition, the system may include a processor that computes an amount of analyte transferred per pumping session.

21 Claims, 9 Drawing Sheets

Related U.S. Application Data continuation-in-part of application No. 17/174,855, filed on Feb. 12, 2021, now Pat. No. 11,602,583, which is a continuation of application No. 15/985, 598, filed on May 21, 2018, now Pat. No. 10,918,778.

(60) Provisional application No. 62/510,652, filed on May 24, 2017.

(51) Int. Cl.

| | |
|---|---|
| *A61K 9/08* | (2006.01) |
| *A61K 31/7004* | (2006.01) |
| *A61K 31/716* | (2006.01) |
| *A61K 33/14* | (2006.01) |
| *A61L 2/00* | (2006.01) |
| *A61M 27/00* | (2006.01) |
| *A61M 31/00* | (2006.01) |
| *A61P 7/08* | (2006.01) |

(52) U.S. Cl.
CPC ............ *A61K 31/716* (2013.01); *A61K 33/14* (2013.01); *A61M 1/287* (2013.01); *A61M 27/002* (2013.01); *A61M 31/002* (2013.01); *A61P 7/08* (2018.01); *A61L 2/0047* (2013.01); *A61L 2202/21* (2013.01); *A61M 2205/18* (2013.01); *A61M 2205/3317* (2013.01); *A61M 2205/3337* (2013.01); *A61M 2205/3344* (2013.01); *A61M 2205/3368* (2013.01); *A61M 2205/3379* (2013.01); *A61M 2205/3569* (2013.01); *A61M 2205/3576* (2013.01); *A61M 2205/502* (2013.01); *A61M 2205/52* (2013.01); *A61M 2205/587* (2013.01); *A61M 2205/6009* (2013.01); *A61M 2205/70* (2013.01); *A61M 2205/8206* (2013.01); *A61M 2205/8243* (2013.01); *A61M 2209/086* (2013.01); *A61M 2209/088* (2013.01); *A61M 2210/1017* (2013.01); *A61M 2210/1085* (2013.01)

(58) Field of Classification Search
CPC ........ A61M 31/002; A61M 2210/1017; A61M 2210/1085; A61K 9/0019; A61K 9/08; A61K 31/7004; A61K 31/716
See application file for complete search history.

(56) References Cited

U.S. PATENT DOCUMENTS

| | | | |
|---|---|---|---|
| 3,540,451 | A | 11/1970 | Zeman et al. |
| 3,575,158 | A | 4/1971 | Summers |
| 3,608,088 | A | 9/1971 | Dorman et al. |
| 3,626,950 | A | 12/1971 | Schulte |
| 3,642,004 | A | 2/1972 | Osthagen et al. |
| 3,654,932 | A | 4/1972 | Newkirk et al. |
| 3,669,116 | A | 6/1972 | Heyer |
| 3,810,259 | A | 5/1974 | Summers |
| 3,910,283 | A | 10/1975 | Leveen |
| 4,014,346 | A | 3/1977 | Brownlee et al. |
| 4,083,786 | A | 4/1978 | Tsuda et al. |
| 4,240,434 | A | 12/1980 | Newkirk |
| 4,261,341 | A | 4/1981 | Hakim et al. |
| 4,347,543 | A | 8/1982 | Frister et al. |
| 4,354,933 | A | 10/1982 | Lester |
| 4,368,737 | A | 1/1983 | Ash |
| 4,398,910 | A | 8/1983 | Blake et al. |
| 4,416,657 | A | 11/1983 | Berglund |
| 4,418,693 | A | 12/1983 | LeVeen et al. |
| 4,419,094 | A | 12/1983 | Patel |
| 4,465,481 | A | 8/1984 | Blake |
| 4,468,219 | A | 8/1984 | George et al. |
| 4,475,898 | A | 10/1984 | Brodner et al. |
| 4,475,899 | A | 10/1984 | Muller |
| 4,490,137 | A | 12/1984 | Moukheibir |
| 4,553,956 | A | 11/1985 | Muller |
| 4,557,724 | A | 12/1985 | Gregonis et al. |
| 4,584,994 | A | 4/1986 | Bamberger et al. |
| 4,594,631 | A | 6/1986 | Iwaki |
| 4,595,390 | A | 6/1986 | Hakim et al. |
| 4,610,625 | A | 9/1986 | Bunn |
| 4,610,658 | A | 9/1986 | Buchwald et al. |
| 4,615,691 | A | 10/1986 | Hakim et al. |
| 4,618,343 | A | 10/1986 | Polaschegg |
| 4,632,435 | A | 12/1986 | Polyak |
| 4,650,463 | A | 3/1987 | LeVeen et al. |
| 4,657,530 | A | 4/1987 | Buchwald et al. |
| 4,687,471 | A | 8/1987 | Twardowski et al. |
| 4,690,673 | A | 9/1987 | Bloomquist |
| 4,725,207 | A | 2/1988 | Buchwald et al. |
| 4,772,257 | A | 9/1988 | Hakim et al. |
| 4,779,614 | A | 10/1988 | Moise |
| 4,784,638 | A | 11/1988 | Ghajar et al. |
| 4,850,955 | A | 7/1989 | Newkirk |
| D303,840 | S | 10/1989 | Weilbacher |
| 4,880,414 | A | 11/1989 | Whipple |
| 4,886,789 | A | 12/1989 | Milner |
| 4,904,236 | A | 2/1990 | Redmond et al. |
| 4,950,232 | A | 8/1990 | Ruzicka et al. |
| 4,963,129 | A | 10/1990 | Rusch |
| 4,963,133 | A | 10/1990 | Whipple |
| 4,991,594 | A | 2/1991 | Angelchik |
| 5,011,472 | A | 4/1991 | Aebischer et al. |
| 5,021,048 | A | 6/1991 | Buckholtz |
| 5,037,385 | A | 8/1991 | O'Byrne |
| 5,045,057 | A | 9/1991 | Van Driessche et al. |
| 5,057,075 | A | 10/1991 | Moncrief et al. |
| 5,071,408 | A | 12/1991 | Ahmed |
| 5,078,688 | A | 1/1992 | Lobodzinski et al. |
| 5,141,493 | A | 8/1992 | Jacobsen et al. |
| 5,147,281 | A | 9/1992 | Thornton et al. |
| 5,167,615 | A | 12/1992 | East et al. |
| 5,180,387 | A | 1/1993 | Ghajar et al. |
| 5,254,084 | A | 10/1993 | Geary |
| 5,356,386 | A | 10/1994 | Goldberg et al. |
| 5,360,414 | A | 11/1994 | Yarger |
| 5,385,541 | A | 1/1995 | Kirsch et al. |
| 5,387,188 | A | 2/1995 | Watson |
| 5,387,192 | A | 2/1995 | Glantz et al. |
| 5,391,143 | A | 2/1995 | Kensey |
| 5,395,320 | A | 3/1995 | Padda et al. |
| 5,395,350 | A | 3/1995 | Summers |
| 5,397,354 | A | 3/1995 | Wilk et al. |
| 5,431,637 | A | 7/1995 | Okada et al. |
| 5,472,323 | A | 12/1995 | Hirabayashi et al. |
| 5,474,683 | A | 12/1995 | Bryant et al. |
| 5,489,276 | A | 2/1996 | Jamshidi |
| 5,520,632 | A | 5/1996 | Leveen et al. |
| 5,549,579 | A | 8/1996 | Batdorf et al. |
| 5,575,770 | A | 11/1996 | Melsky et al. |
| 5,589,197 | A | * 12/1996 | Shockley ............... A61K 33/14<br>514/23 |
| 5,593,394 | A | 1/1997 | Kanesaka et al. |
| 5,629,025 | A | 5/1997 | Shockley et al. |
| 5,631,025 | A | 5/1997 | Shockley et al. |
| 5,637,083 | A | 6/1997 | Bertrand et al. |
| 5,676,670 | A | 10/1997 | Kim |
| 5,713,864 | A | 2/1998 | Verkaart |
| 5,725,506 | A | 3/1998 | Freeman et al. |
| 5,788,468 | A | 8/1998 | Dewa et al. |
| 5,830,172 | A | 11/1998 | Leveen et al. |
| 5,902,336 | A | 5/1999 | Mishkin |
| 5,944,684 | A | 8/1999 | Roberts et al. |
| 5,945,449 | A | 8/1999 | Purcell et al. |
| 5,947,911 | A | 9/1999 | Wong et al. |
| 5,980,478 | A | 11/1999 | Gorsuch et al. |
| 5,980,480 | A | 11/1999 | Rubenstein et al. |
| 5,989,207 | A | 11/1999 | Hughes |
| 6,007,511 | A | 12/1999 | Prywes |
| 6,017,355 | A | 1/2000 | Hessel et al. |
| D420,738 | S | 2/2000 | Carter et al. |
| 6,022,333 | A | 2/2000 | Kensey |
| 6,027,442 | A | 2/2000 | Von Iderstein |

(56) References Cited

U.S. PATENT DOCUMENTS

| | | | |
|---|---|---|---|
| 6,042,569 A | 3/2000 | Finch, Jr. et al. |
| 6,099,513 A | 8/2000 | Spehalski |
| 6,132,405 A | 10/2000 | Nilsson et al. |
| 6,132,415 A | 10/2000 | Finch et al. |
| 6,146,354 A | 11/2000 | Beil |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,234,964 B1 | 5/2001 | Iliff |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,478,789 B1 | 11/2002 | Spehalski et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,648,906 B2 | 11/2003 | Lasheras et al. |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgesen |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,966,889 B2 | 11/2005 | Saab |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,986,752 B2 | 1/2006 | McGuckin, Jr. et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,118,857 B2 | 10/2006 | Martis et al. |
| 7,128,735 B2 | 10/2006 | Weston |
| 7,169,303 B2 | 1/2007 | Sullivan et al. |
| 7,195,608 B2 | 3/2007 | Burnett |
| D558,338 S | 12/2007 | Itoh |
| D558,341 S | 12/2007 | Fujiwara et al. |
| D558,342 S | 12/2007 | Fujiwara et al. |
| 7,311,690 B2 | 12/2007 | Burnett |
| 7,335,179 B2 | 2/2008 | Burnett |
| 7,379,885 B1 | 5/2008 | Zakim |
| 7,419,483 B2 | 9/2008 | Shehada |
| 7,544,301 B2 | 6/2009 | Shah et al. |
| 7,621,886 B2 | 11/2009 | Burnett |
| 7,670,332 B2 | 3/2010 | O'Keefe et al. |
| 7,909,790 B2 | 3/2011 | Burnett |
| 8,012,118 B2 | 9/2011 | Curtin et al. |
| 8,041,419 B2 | 10/2011 | Giftakis et al. |
| 8,202,248 B2 | 6/2012 | Burnett et al. |
| 8,241,239 B2 | 8/2012 | Solomon et al. |
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,600,517 B2 | 12/2013 | Forsell |
| 8,612,013 B2 | 12/2013 | Forsell |
| 8,641,659 B2 | 2/2014 | Soykan et al. |
| 8,704,484 B2 | 4/2014 | Rosik et al. |
| 8,771,221 B2 | 7/2014 | Burnett |
| 8,882,699 B2 | 11/2014 | Burnett |
| 8,961,448 B2 | 2/2015 | Forsell |
| 8,965,523 B2 | 2/2015 | Forsell |
| 8,992,456 B1 | 3/2015 | Powell |
| 9,039,652 B2 | 5/2015 | Degen et al. |
| 9,138,521 B2 | 9/2015 | Solomon et al. |
| 9,138,523 B2 | 9/2015 | Burnett et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,381,301 B2 | 7/2016 | Lattanzio et al. |
| 9,421,347 B2 | 8/2016 | Burnett |
| 9,440,017 B2 | 9/2016 | Rohde et al. |
| 9,577,459 B2 | 2/2017 | Degen et al. |
| 9,673,527 B2 | 6/2017 | Yoon et al. |
| 9,675,327 B2 | 6/2017 | Johnson et al. |
| 9,694,165 B2 | 7/2017 | Forsell |
| 9,808,634 B2 | 11/2017 | Forsell |
| 9,913,968 B2 | 3/2018 | Burnett |
| 9,956,336 B2 | 5/2018 | Degen et al. |
| 10,252,037 B2 | 4/2019 | Degen et al. |
| 10,363,353 B2 | 7/2019 | Lo et al. |
| 10,398,824 B2 | 9/2019 | Burnett et al. |
| 10,569,003 B2 | 2/2020 | Degen et al. |
| 10,716,922 B2 | 7/2020 | Degen et al. |
| 10,744,254 B1 | 8/2020 | Lindo et al. |
| 10,769,244 B2 | 9/2020 | Degen et al. |
| 10,806,344 B2 | 10/2020 | Goetz |
| 10,898,631 B2 | 1/2021 | Inhaber et al. |
| 10,918,778 B2 | 2/2021 | Inhaber et al. |
| 10,964,417 B2 | 3/2021 | Gassman et al. |
| 11,235,131 B2 | 2/2022 | Degen et al. |
| 11,464,891 B2 | 10/2022 | Crosbie et al. |
| 11,559,618 B2 | 1/2023 | Testani et al. |
| 11,602,583 B2 | 3/2023 | Inhaber et al. |
| 11,793,916 B2 | 10/2023 | Degen et al. |
| 11,839,712 B2 | 12/2023 | Burnett et al. |
| 11,844,890 B2 | 12/2023 | Testani et al. |
| 11,854,697 B2 | 12/2023 | Degen et al. |
| 2001/0025170 A1 | 9/2001 | Paderni |
| 2001/0027289 A1 | 10/2001 | Treu et al. |
| 2002/0013545 A1 | 1/2002 | Soltanpour et al. |
| 2002/0022793 A1 | 2/2002 | Bertrand et al. |
| 2002/0091352 A1 | 7/2002 | McGuckin, Jr. et al. |
| 2002/0107467 A1 | 8/2002 | Levin |
| 2002/0123715 A1 | 9/2002 | Sorenson et al. |
| 2003/0004495 A1 | 1/2003 | Saul |
| 2003/0114787 A1 | 6/2003 | Gura |
| 2003/0114898 A1 | 6/2003 | Von Arx et al. |
| 2003/0163079 A1 | 8/2003 | Burnett |
| 2003/0171710 A1 | 9/2003 | Bassuk et al. |
| 2003/0216677 A1* | 11/2003 | Pan ...................... A61M 1/154 |
| | | 210/252 |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0060865 A1 | 4/2004 | Callan et al. |
| 2004/0098113 A1 | 5/2004 | Forsell et al. |
| 2004/0106205 A1 | 6/2004 | Stevenson et al. |
| 2004/0121982 A1 | 6/2004 | Martis et al. |
| 2004/0126775 A1 | 7/2004 | Altieri et al. |
| 2004/0147871 A1 | 7/2004 | Burnett |
| 2005/0036983 A1 | 2/2005 | Simon et al. |
| 2005/0075700 A1 | 4/2005 | Schommer et al. |
| 2005/0096582 A1 | 5/2005 | Burnett |
| 2005/0119598 A1 | 6/2005 | Callan et al. |
| 2005/0131340 A1 | 6/2005 | Sorenson et al. |

(56) References Cited

U.S. PATENT DOCUMENTS

| | | | |
|---|---|---|---|
| 2005/0273034 A1 | 12/2005 | Burnett | |
| 2005/0276868 A1 | 12/2005 | Degreve et al. | |
| 2006/0010014 A1 | 1/2006 | Brown | |
| 2006/0024200 A1 | 2/2006 | Nishikiori et al. | |
| 2006/0036208 A1 | 2/2006 | Burnett | |
| 2006/0058731 A1 | 3/2006 | Burnett et al. | |
| 2006/0094984 A1 | 5/2006 | Wood et al. | |
| 2007/0055197 A1 | 3/2007 | Shakir | |
| 2007/0106205 A1 | 5/2007 | Connell et al. | |
| 2007/0208323 A1 | 9/2007 | Gregorich et al. | |
| 2007/0228071 A1 | 10/2007 | Kamen et al. | |
| 2007/0233042 A1 | 10/2007 | Moehle et al. | |
| 2007/0255345 A1 | 11/2007 | Krause | |
| 2007/0299317 A1 | 12/2007 | Hoyme et al. | |
| 2008/0024294 A1 | 1/2008 | Mazar | |
| 2008/0108935 A1 | 5/2008 | Nyhart, Jr. | |
| 2008/0129486 A1 | 6/2008 | Jeckelmann et al. | |
| 2008/0154173 A1 | 6/2008 | Burnett | |
| 2008/0214983 A1 | 9/2008 | Mauge et al. | |
| 2008/0230450 A1 | 9/2008 | Burbank et al. | |
| 2009/0054874 A1 | 2/2009 | Barron et al. | |
| 2009/0062887 A1 | 3/2009 | Mass et al. | |
| 2009/0069642 A1 | 3/2009 | Gao et al. | |
| 2009/0171241 A1 | 7/2009 | Garcia et al. | |
| 2009/0198174 A1 | 8/2009 | Childers et al. | |
| 2009/0222065 A1 | 9/2009 | Dlugos, Jr. et al. | |
| 2009/0275805 A1 | 11/2009 | Lane et al. | |
| 2009/0275924 A1 | 11/2009 | Lattanzio et al. | |
| 2009/0304600 A1 | 12/2009 | Shetty | |
| 2009/0318844 A1 | 12/2009 | Burnett | |
| 2010/0010832 A1 | 1/2010 | Boute et al. | |
| 2010/0022902 A1 | 1/2010 | Lee et al. | |
| 2010/0114012 A1 | 5/2010 | Sandford et al. | |
| 2010/0185225 A1 | 7/2010 | Albrecht et al. | |
| 2010/0215375 A1 | 8/2010 | Reams | |
| 2010/0222846 A1 | 9/2010 | Goetz | |
| 2010/0234793 A1 | 9/2010 | Dacey, Jr. et al. | |
| 2010/0241052 A1 | 9/2010 | Dacey, Jr. et al. | |
| 2010/0249692 A1 | 9/2010 | Dacey, Jr. et al. | |
| 2010/0270970 A1 | 10/2010 | Toya et al. | |
| 2010/0312163 A1 | 12/2010 | Forsell | |
| 2010/0312164 A1 | 12/2010 | Forsell | |
| 2011/0025261 A1 | 2/2011 | Bersenev | |
| 2011/0034986 A1 | 2/2011 | Chou et al. | |
| 2011/0163714 A1 | 7/2011 | Ettes et al. | |
| 2011/0172545 A1 | 7/2011 | Grudic et al. | |
| 2011/0184339 A1 | 7/2011 | Tan | |
| 2011/0184340 A1 | 7/2011 | Tan et al. | |
| 2011/0202041 A1 | 8/2011 | Forsell | |
| 2011/0245665 A1 | 10/2011 | Nentwick | |
| 2011/0291613 A1 | 12/2011 | Rosik et al. | |
| 2012/0032522 A1 | 2/2012 | Schatz et al. | |
| 2012/0035255 A1 | 2/2012 | Fanelli et al. | |
| 2012/0041279 A1 | 2/2012 | Freeman et al. | |
| 2012/0191152 A1 | 7/2012 | Kameli | |
| 2012/0199151 A1 | 8/2012 | Haile | |
| 2012/0209085 A1 | 8/2012 | Degen et al. | |
| 2012/0209165 A1 | 8/2012 | Degen et al. | |
| 2012/0235503 A1 | 9/2012 | Kesler et al. | |
| 2012/0235634 A1 | 9/2012 | Hall et al. | |
| 2012/0289881 A1 | 11/2012 | Lyu et al. | |
| 2013/0138452 A1 | 5/2013 | Cork et al. | |
| 2013/0187619 A1 | 7/2013 | Dunipace | |
| 2013/0197428 A1 | 8/2013 | Cruz | |
| 2013/0199998 A1 | 8/2013 | Kelly et al. | |
| 2013/0211322 A1* | 8/2013 | Degen | A61M 1/285 604/29 |
| 2013/0289334 A1 | 10/2013 | Badstibner et al. | |
| 2013/0303971 A1 | 11/2013 | Budgett et al. | |
| 2013/0317476 A1 | 11/2013 | Searle et al. | |
| 2014/0005743 A1 | 1/2014 | Giuffrida et al. | |
| 2014/0012180 A1 | 1/2014 | Levin et al. | |
| 2014/0018727 A1 | 1/2014 | Burbank et al. | |
| 2014/0066841 A1 | 3/2014 | Degen et al. | |
| 2014/0074180 A1 | 3/2014 | Heldman et al. | |
| 2014/0098627 A1 | 4/2014 | Mochizuki et al. | |
| 2014/0121487 A1 | 5/2014 | Faybishenko et al. | |
| 2014/0121590 A1 | 5/2014 | Degen | |
| 2014/0158623 A1* | 6/2014 | Pudil | A61M 1/3472 210/96.2 |
| 2014/0200481 A1 | 7/2014 | Johnson et al. | |
| 2014/0213966 A1 | 7/2014 | Ostapoff et al. | |
| 2014/0266022 A1 | 9/2014 | Degen et al. | |
| 2014/0275727 A1 | 9/2014 | Bonde et al. | |
| 2014/0275827 A1 | 9/2014 | Gill et al. | |
| 2014/0330147 A1 | 11/2014 | Ousdigian et al. | |
| 2015/0019257 A1 | 1/2015 | Doyle et al. | |
| 2015/0088090 A1 | 3/2015 | Macy, Jr. | |
| 2015/0250427 A1 | 9/2015 | Soykan et al. | |
| 2015/0342872 A1 | 12/2015 | Williamson et al. | |
| 2016/0000984 A1 | 1/2016 | Burnett et al. | |
| 2016/0022971 A1 | 1/2016 | Degen et al. | |
| 2016/0087687 A1 | 3/2016 | Kesler et al. | |
| 2016/0151553 A1 | 6/2016 | Bonde | |
| 2016/0183819 A1 | 6/2016 | Burnett et al. | |
| 2016/0303313 A1 | 10/2016 | Burke et al. | |
| 2016/0331947 A1 | 11/2016 | Burnett | |
| 2017/0079760 A1 | 3/2017 | Newman et al. | |
| 2017/0128654 A1 | 5/2017 | Feld | |
| 2017/0136221 A1 | 5/2017 | Budgett et al. | |
| 2017/0173262 A1 | 6/2017 | Veltz | |
| 2017/0216611 A1 | 8/2017 | Yoder et al. | |
| 2017/0245794 A1 | 8/2017 | Sharma et al. | |
| 2017/0281846 A1* | 10/2017 | Manda | A61K 31/19 |
| 2017/0281848 A1 | 10/2017 | Axelsson et al. | |
| 2017/0304597 A1 | 10/2017 | Forsell | |
| 2017/0312530 A1 | 11/2017 | Schilling et al. | |
| 2018/0043079 A1 | 2/2018 | Gerber et al. | |
| 2018/0056050 A1 | 3/2018 | Degen et al. | |
| 2018/0060520 A1 | 3/2018 | Degen et al. | |
| 2018/0093081 A1 | 4/2018 | Forsell | |
| 2018/0126130 A1 | 5/2018 | Nitzan et al. | |
| 2018/0243495 A1 | 8/2018 | Degen et al. | |
| 2018/0338914 A1 | 11/2018 | Inhaber et al. | |
| 2018/0344917 A1 | 12/2018 | Inhaber et al. | |
| 2019/0232029 A1 | 8/2019 | Degen et al. | |
| 2020/0054813 A1 | 2/2020 | Burnett et al. | |
| 2020/0160057 A1 | 5/2020 | Roxas et al. | |
| 2020/0188569 A1 | 6/2020 | Degen et al. | |
| 2021/0134431 A1 | 5/2021 | Garcia et al. | |
| 2021/0187179 A1 | 6/2021 | Inhaber et al. | |
| 2021/0244381 A1 | 8/2021 | Sweeney et al. | |
| 2022/0126072 A1 | 4/2022 | Crosbie et al. | |
| 2023/0001065 A1 | 1/2023 | Wirth et al. | |

FOREIGN PATENT DOCUMENTS

| | | |
|---|---|---|
| CN | 102024090 A | 4/2011 |
| CN | 201930383 U | 8/2011 |
| CN | 104077464 A | 10/2014 |
| CN | 104994894 A | 10/2015 |
| EP | 0366389 A2 | 5/1990 |
| EP | 0980685 A2 | 2/2000 |
| EP | 1362605 A1 | 11/2003 |
| EP | 1517718 A1 | 3/2005 |
| EP | 1539294 A1 | 6/2005 |
| EP | 1517718 B1 | 10/2010 |
| EP | 2244662 A1 | 11/2010 |
| EP | 2244663 A1 | 11/2010 |
| EP | 2244667 A1 | 11/2010 |
| EP | 2244758 A1 | 11/2010 |
| EP | 2244759 A1 | 11/2010 |
| EP | 2244760 A1 | 11/2010 |
| EP | 1539294 B1 | 1/2011 |
| EP | 2676638 A1 | 12/2013 |
| EP | 2349473 B1 | 12/2016 |
| EP | 2676638 B1 | 7/2017 |
| EP | 3275505 A1 | 1/2018 |
| EP | 2054105 B1 | 7/2018 |
| GB | 2350794 A | 12/2000 |
| JP | S63143074 A | 6/1988 |
| JP | H04327857 A | 11/1992 |
| JP | H0956810 A | 3/1997 |
| JP | 2000072658 A | 3/2000 |

(56)                    References Cited

FOREIGN PATENT DOCUMENTS

| JP | 2000510552 A | 8/2000 |
| JP | 2004513681 A | 5/2004 |
| JP | 2005171892 A | 6/2005 |
| JP | 2005534400 A | 11/2005 |
| JP | 2006507018 A | 3/2006 |
| JP | 2010527247 A | 8/2010 |
| WO | WO-9741799 A1 | 11/1997 |
| WO | WO-9816171 A1 | 4/1998 |
| WO | WO-9934116 A1 | 7/1999 |
| WO | WO-0057833 A1 | 10/2000 |
| WO | WO-0207596 A1 | 1/2002 |
| WO | WO-03072166 A1 | 9/2003 |
| WO | WO-2004012806 A1 | 2/2004 |
| WO | WO-2004105730 A1 | 12/2004 |
| WO | WO-2005018708 A2 | 3/2005 |
| WO | WO-2006023589 A2 | 3/2006 |
| WO | WO-2008055248 A2 | 5/2008 |
| WO | WO-2009091267 A2 | 7/2009 |
| WO | WO-2009096854 A1 | 8/2009 |
| WO | WO-2010077851 A2 | 7/2010 |
| WO | WO-2012078230 A1 | 6/2012 |
| WO | WO-2012112664 A1 | 8/2012 |
| WO | WO-2013122580 A1 | 8/2013 |
| WO | WO-2013166038 A2 | 11/2013 |
| WO | WO-2014064053 A2 | 5/2014 |
| WO | WO-2014140277 A1 | 9/2014 |
| WO | WO-2015082555 A1 | 6/2015 |
| WO | WO-2015108782 A1 | 7/2015 |
| WO | WO-2017034452 A1 | 3/2017 |
| WO | WO-2017176687 A1 | 10/2017 |
| WO | WO-2018037359 A1 | 3/2018 |
| WO | WO-2018065945 A1 | 4/2018 |
| WO | WO-2018215917 A1 | 11/2018 |

OTHER PUBLICATIONS

International Search Report & Written Opinion dated Mar. 30, 2023 in Int'l PCT Patent Appl. Serial No. PCT/IB2022/062709 (2110).
International Search Report & Written Opinion dated Jun. 14, 2023 in Int'l PCT Patent Appl. No. PCT/IB2023/050999 (1810).
International Search Report & Written Opinion dated Jun. 27, 2023 in Int'l PCT Patent Appl. No. PCT/IB2023/054061 (2010).
McKinnie, et al., Long-term Therapy for Heart Failure With Continuous Ambulatory Peritoneal Dialysis, Archives of Internal Medicine, 145(6):1128-9 (Jun. 1985).
Pharmacology Review(s), Center for Drug Evaluation and Research, Approval Package for: Application No. 21-321, Dec. 14, 2001.
Toxicology Review, NDA No. 21-321, Aug. 2001.
U.S. Appl. No. 15/985,598 / U.S. Pat. No. 10,918,778, filed May 21, 2018 / Feb. 16, 2021.
U.S. Appl. No. 15/985,617 / U.S. Pat. No. 10,898,631, filed May 21, 2018 / Jan. 26, 2021.
U.S. Appl. No. 16/378,376 / U.S. Pat. No. 11,235,131, filed Apr. 8, 2019 / Feb. 1, 2022.
U.S. Appl. No. 16/550,035, filed Aug. 23, 2019.
U.S. Appl. No. 16/784,106, filed Feb. 6, 2020.
U.S. Appl. No. 17/013,806, filed Sep. 7, 2020.
U.S. Appl. No. 17/174,855, filed Feb. 12, 2021.
U.S. Appl. No. 17/646,858, filed Jan. 3, 2022.
U.S. Appl. No. 17/650,183 / U.S. Pat. No. 11,464,891, filed Feb. 7, 2022 / Oct. 11, 2022.
U.S. Appl. No. 17/661,737, filed May 2, 2022.
U.S. Appl. No. 17/930,064, filed Sep. 6, 2022.
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Aminde et al., "Current diagnostic and treatment strategies for Lutembacher syndrome: the pivotal role of echocardiography," Cardiovasc Diagn Ther., 5(2):122-132 (2015).

Ando, et al., Left ventricular decompression through a patent foramen ovale in a patient with hypertrophic cardiomyopathy: A case report, Cardiovascular Ultrasound, 2: 1-7 (2004).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Bellot, et al., Automated Low Flow Pump System for the Treatment of Refractory Ascites: A Multi-Center Safety and Efficacy Study, Journal of Hepatology, 58(5):922-927 (2013).
Benza et al., "Monitoring Pulmonary Arterial Hypertension Using an Implantable Hemodynamic Sensor," Chest, 156(6):1176-1186 (2019).
Ciarka et al., "Atrial Septostomy Decreases Sympathetic Overactivity in Pulmonary Arterial Hypertension," Chest, 131(6):P1831-1837 (2007) (Abstract Only).
Costanzo, et al., Early Ultrafiltration in Patients with Decompensated Heart Failure and Diuretic Resistance, J. Am. Coll. Cardiol., 46(11):2047-2051 (2005).
Davies et al., "Abnormal left heart function after operation for atrial septal defect," British Heart Journal, 32:747-753 (1970).
Doty, et al., Effect of Increased Renal Venous Pressure on Renal Function, J. Trauma., 47(6):1000-1003 (1999).
Extended European Search Report dated May 7, 2021 in EP Patent Appl. Serial No. 20215794.7 (1531).
Extended European Search Report dated Jun. 6, 2012 in EP Patent Appl. Serial No. EP05786343.3, 6 pages (0330).
Extended European Search Report dated Sep. 18, 2019 in EP Patent Appl. Serial No. 19172235.4 (0831).
Extended European Search Report dated Sep. 14, 2011 in EP Patent Appl. Serial No. EP11172759.0, 6 pages (0231).
Extended European Search Report dated Sep. 26, 2011 in EP Patent Appl. Serial No. EP07844792.7, 6 pages (0730).
Francois, et al., Peritoneal Dialysis for Chronic Congestive Heart Failure, Blood Purif., 40(1):45-52 (2015).
Fukuda, et al., Survivin, a Cancer Target with an Emerging Role in Normal Adult Tissues, Mol. Cancer Ther., 5(5):1087-1098 (2006).
Greitz, et al., Pulsatile Brain Movement and Associated Hydrodynamics Studied by Magnetic Resonance Phase Imaging, Diagnostic Neuroradiology, 34(5): 370-380 (1992).
Hanson, et al., Sodium in the dermis colocates to glycosaminoglycan scaffold, with diminishment in type 2 diabetes mellitus, JCI Insight, 6(12):e145470 (2021).
Hecking, et al., Sodium Setpoint and Sodium Gradient: Influence on Plasma Sodium Change and Weight Gain, Am J. Nephrol, 33(1):39-48 (2011).
Houlberg, et al., Terminal Right Heart Failure Due to Complex Congenital Cardiac Disease Successfully Managed by Home Peritoneal Drainage, Cardiol. Young, 13: 568-570 (2003).
International Search Report & Written Opinion dated Jul. 3, 2012 in Int'l PCT Patent Appl No. PCT/US12/25212, 34 pages (0810).
International Search Report & Written Opinion dated Apr. 15, 2008 in Int'l PCT Patent Appl No. PCT/US07/83261, 6 pages (0710).
International Search Report & Written Opinion dated Sep. 28, 2005 in Int'l PCT Patent Appl No. PCT/US04/26781, 4 pages (0410).
International Search Report & Written Opinion dated Apr. 16, 2015 in Int'l PCT Patent Appl. No. PCT/US2015/010840 (1610).
International Search Report & Written Opinion dated Mar. 18, 2013 in Intl PCT Appl. No. PCT/US2012/025188 (0910).
International Search Report & Written Opinion dated Jan. 4, 2018 in Intl PCT Patent Appl. U.S. Appl. No. PCT/IB2017/055092 (1410).
International Search Report and Written Opinion dated Feb. 2, 2018 in Intl PCT Patent Appl. No. PCT/IB2017/055093 (1710).
International Search Report dated Jul. 17, 2003, PCT/US03/05145, 3 pages (0210).
International Search Report dated Sep. 16, 2008, in Intl PCT Patent Appl. No. PCT/US2005/029305, 4 pages (0310).
Int'l Search Report and Written Opinion dated Aug. 24, 2018 in Int'l PCT Patent Appl. Serial No. PCT/IB2018/053587 (1510).
Kenny., Intra-Abdominal Pressure and Renal Function: the Venous Side of the Road, PulmCCM, Critical Care, Gi and Nutrition, Jul.

(56) References Cited

OTHER PUBLICATIONS 14, 2016, accessed on line on Mar. 27, 2017 at http://pulmccm.org/main/2016/critical-care-review/intra-abdominal-pressur-e-renal-function/.

Kulkarni et al., "Lutembacher's syndrome," J Cardiovasc Did Res., 3(2):179-181 (2012).

Kurzyna et al., "Atrial Septostomy in Treatment of End-Stage Right Heart Failure in Patients With Pulmonary Hypertension," Chest, 131:977-983 (2007).

McCausland, et al., Dialysate Sodium, Serum Sodium and Mortality in Maintenance Hemodialysis, 27(4):1613-1618 (2012).

Medtronic Reveal LinqTM LNQ11, Insertable Cardiac Monitor, Clinician Manual, 98 pages (2015).

Munoz, et al., Dialysate Sodium and Sodium Gradient in Maintenance Hemodialysis: a Neglected Sodium Restriction Approach? Nephrol Dial Transplant, 26(4):1281-1287 (2011).

Nakayama, et al., Clinical Effect of Low Na Concentration Dialysate (120mEq/L) for CAPD Patients, Abstracts of the XIII Annual CAPD Conference, Peritoneal Dialysis International, 13(Supplement 1), (1993).

Neragi-Miandoab., Malignant Pleural Effusion, Current and Evolving Approaches for its Diagnosis and Management, Lung Cancer 54:1-9(2006).

Ortiz, et al., Long-Term Automated Peritoneal Dialysis in Patients with Refractory Congestive Heart Failure, Advances in Peritoneal Dialysis, 19:77-80 (2003).

PCT International Search Report and Written Opinion dated Aug. 19, 2014 in PCT Patent Application No. PCT/EP2014/055104 (1310).

Peters et al., "Self-fabricated fenestrated Amplatzer occluders for transcatheter closure of atrial septal defect in patients with left ventricular restriction: midterm results," Clin Res Cardiol., 95:88-92 (2006).

Puttagunta, et al., Peritoneal Dialysis for Heart Failure, Peritoneal Dialysis International, 35(6):645-649 (2015).

Rao, et al., "First-in-Human Experience With Peritoneal Direct Sodium Removal Using A Zero-Sodium Solution," A New Candidate Therapy for Volume Overload, Circulation, vol. 141, 2020, pp. 1043-1053.

Rosenblit, et al., "Peritoneal-Urinary Drainage for Treatment of Refractory Ascites: A Pilot Study," Nov./Dec. 1998, Journal of Vascular and Interventional Radiology, 9(6):998-1005,(1998).

Rosenblum, et al., Conceptual Considerations For Device-Based Therapy in Acute Decompensated Heart Failure, *Circulation: Heart Failure*, 13(4):e006731 (Apr. 2020).

Ross et al., "Interatrial Communication and Left Atrial Hypertension—A Cause of Continuous Murmur," Circulation, 28:853-860 (1963).

Ruhi, et al., Use of Peritoneal Ultrafiltration in the Elderly Refractory Congestive Heart Failure Patients, Int. Urol. and Nephrol., 44(3):963-969 (2012).

Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).

Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).

Second Written Opinion dated May 16, 2019 in Int'l PCT Patent Appl. No. PCT/IB2018/053587 (1510).

Smyth, Chris, Pump implant for Cancer Patients 'is a Game-Changer' for Thousands, the Times, Health News, Jan. 18, 2013 (p. 11).

Sort, et al., Effect of Intravenous Albumin on Renal Impairment and Mortality in Patients with Cirrhosis and Spontaneous Bacterial Peritonitis, The New England Journal of Medicine, 341(6):403-409 (Aug. 5, 1999).

Supplementary European Search Report dated Jun. 4, 2010 in EP Patent Appl. Serial No. EP03719316.6, 3 pages (0230).

Tan et al., The Evidence on the Effectiveness of Management for Malignant Pleural Effusion: A Systematic Review, European Journal of Cardio-thoracic Surgery 29, 2006 (pp. 829-838).

Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).

Toto R.D., "Leveraging the Peritoneal as a New Diuretic Strategy for Heart Failure," Circulation, vol. 141, 2020, pp. 1054-1056.

Viaene et al., "Pulmonary oedema after percutaneous ASD-closure," Acta Cardiol., 65(2):257-260 (2010).

Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).

Warren, et al., Management of Malignant Pleural Effusions Using the Pleurx Catheter, Ann. Thrac. Sur. 85, 2008, (pp. 1049-1055).

Webb et al., "Atrial Septal Defects in the Adult Recent Progress and Overview," Circulation, 114:1645-1653 (2006).

Wiedemann, H.R., "Earliest description by Johann Friedrich Meckel, Senior (1750) of what is known today as Lutembacher syndrome (1916)," Am J Med Genet., 53(1):59-64 (1994) (Abstract Only).

Www.medtronic.com/us-en/patients/treatments-therapies/fainting-heart-monit- or/reveal-linq-icm.html (May 2017) (Accessed Nov. 27, 2017).

Zepeda-Orozco, et al., Dialysis Disequilibrium Syndrome, Pediatr. Nephrol, 27:2205-2211 (2012).

Zhang et al., "Acute left ventricular failure after transcatheter closure of a secundum atrial septal defect in a patient with hypertrophic cardiomyopathy," Chin Med J., 124(4):618-621 (2011).

Aanen et al., A detailed analysis of sodium removal by peritoneal dialysis: comparison with predictions from the three-pore model of membrane function, *Nephrol. Dial. Transplant.*, 20(6):1192-1200 (2005).

Chen et al., Low-dose dopamine or low-dose nesiritide in acute heart failure with renal dysfunction: the ROSE acute heart failure randomized trial. Multicenter Study Randomized Controlled Trial, *JAMA*, 310(23):2533-2543 (2013).

Cox et al., Loop diuretic resistance complicating acute heart failure, *Heart Fail. Rev.*, 25(1):133-145 (2020).

Damman et al., The kidney in heart failure: an update, *Eur. Heart J.*, 36(23):1437-1444 (2015).

Finkelstein et al., Superiority of icodextrin compared with 4.25% dextrose for peritoneal ultrafiltration, *J. Am. Soc. Nephrol.*, 16(2):546-554 (2005).

Fischbach et al., Increasing sodium removal on peritoneal dialysis: applying dialysis mechanics to the peritoneal dialysis prescription, *Kidney Int.*, 89(4):761-766 (2016).

Heidenreich et al., 2022 AHA/ACC/HFSA Guideline for the Management of Heart Failure: A Report of the American College of Cardiology/American Heart Association Joint Committee on Clinical Practice Guidelines, *J. Am. Coll. Cardiol.*, 79(17):e263-e421 (2022).

Hodson et al., Natriuretic Response Is Highly Variable and Associated With 6-Month Survival: Insights From the ROSE-AHF Trial, *JACC Heart Fail.*, 7(5):383-391 (2019).

Hollenberg, et al., 2019 ACC Expert Consensus Decision Pathway on Risk Assessment, Management and Clinical Trajectory of Patients Hospitalized With Heart Failure, *Journal of the American College of Cardiology*, 74(15):1966 (2019).

International Search Report & Written Opinion dated Jan. 10, 2024 in Int'l PCT Patent Appl. Serial No. PCT/IB2023/058117 (2210).

International Search Report & Written Opinion dated Nov. 8, 2023 in Int'l PCT Patent Appl. Serial No. PCT/IB2023/058630 (1910).

Mcdonagh et al., "2021 ESC Guidelines for the diagnosis and treatment of acute and chronic heart failure," *Eur. Heart J.*, 42(36):3599-3726 (2021).

Moberly et al., "Pharmacokinetics of icodextrin in peritoneal dialysis patients," *Kidney Int Suppl.*, (81):S23-33 (2002).

(56)            References Cited

OTHER PUBLICATIONS

Morelle et al., "Mechanisms of Crystalloid versus Colloid Osmosis across the Peritoneal Membrane," *J. Am. Soc. Nephrol.*, 29(7):1875-1886 (2018).

Mullens et al. The use of diuretics in heart failure with congestion—a position statement from the Heart Failure Association of the European Society of Cardiology, *Eur. J. Heart Fail.* 21(2):137-155 (2019).

Rao et al., "Natriuretic Equation to Predict Loop Diuretic Response in Patients With Heart Failure," *J Am Coll Cardiol.* 77(6):695-708 (2021).

Testani et al., "Loop diuretic efficiency: a metric of diuretic responsiveness with prognostic importance in acute decompensated heart failure," *Circ. Heart Fail.*, 7(2):261-270 (2014).

Verbrugge et al., "Altered Hemodynamics and End-Organ Damage in Heart Failure: Impact on the Lung and Kidney," *Circulation*, 142(10):998-1012 (2020).

Wolfson, et al. "A Randomized Controlled Trail to Evaluate the Efficacy and Safety of Icodextrin in Peritoneal Dialysis," Am. J. Kidney Dis., vol. 40(5):1055-1065, (Nov. 2002).

\* cited by examiner

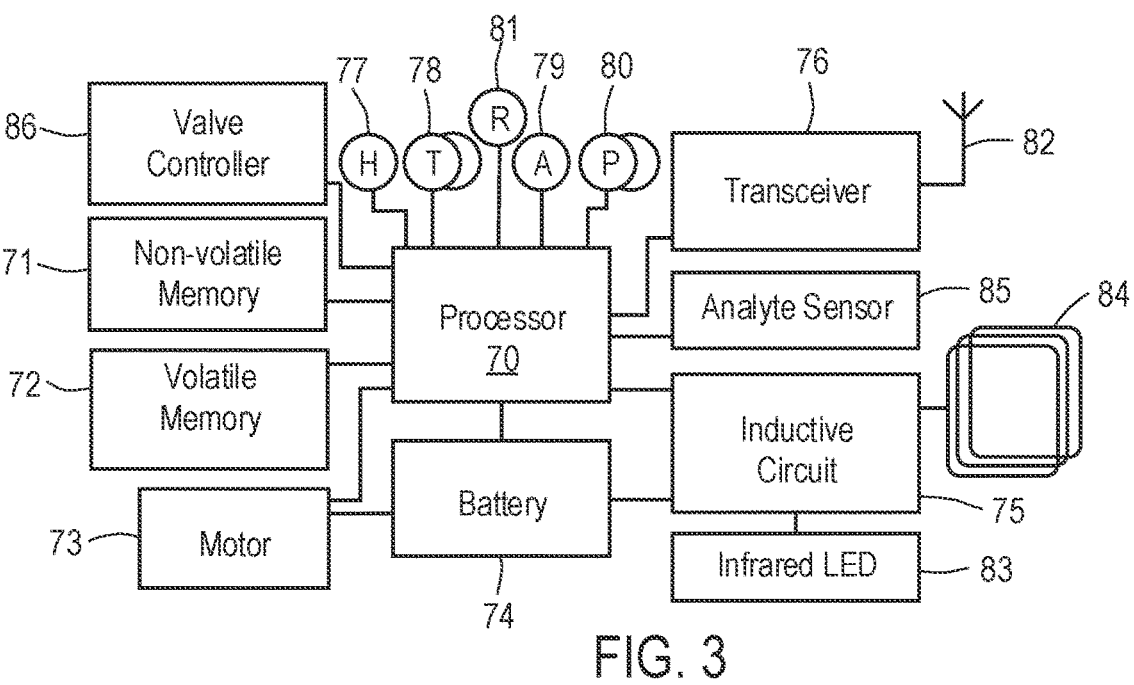
FIG. 3
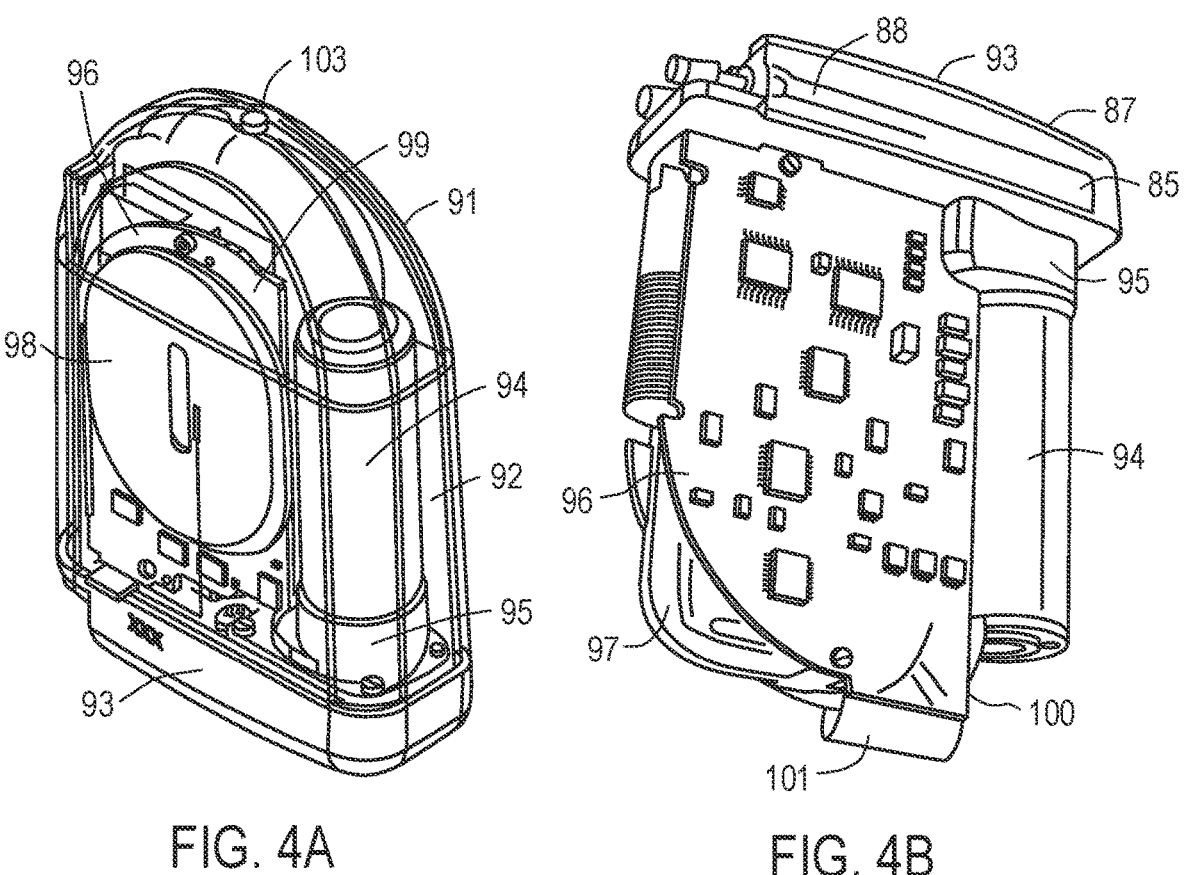
FIG. 4A                    FIG. 4B

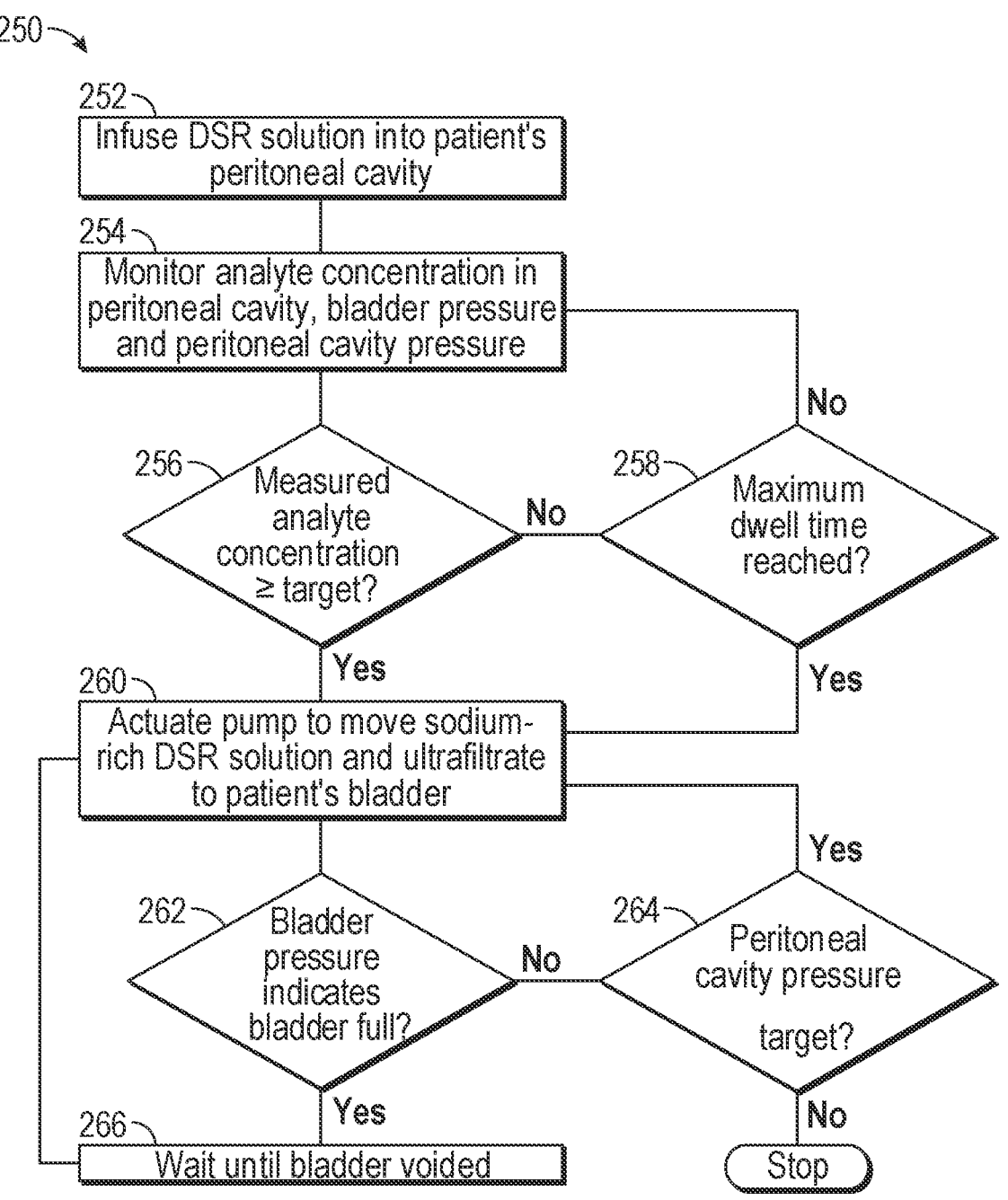

250

252
Infuse DSR solution into patient's peritoneal cavity

254
Monitor analyte concentration in peritoneal cavity, bladder pressure and peritoneal cavity pressure 256
Measured analyte concentration ≥ target?

No

258
Maximum dwell time reached?

No

Yes

Yes

260
Actuate pump to move sodium-rich DSR solution and ultrafiltrate to patient's bladder 262
Bladder pressure indicates bladder full?

No

264
Peritoneal cavity pressure target?

Yes

Yes

No

266
Wait until bladder voided

Stop

FIG. 12

IMPLANTABLE PUMP FOR DIRECT SODIUM REMOVAL THERAPY HAVING ON-BOARD ANALYTE SENSOR

CROSS-REFERENCE TO RELATED APPLICATIONS

This application is a continuation of U.S. patent application Ser. No. 17/650,183, filed Feb. 7, 2022, now U.S. Pat. No. 11,464,891, which is a continuation-in-part of U.S. patent application Ser. No. 17/174,855, filed Feb. 12, 2021, which is a continuation of U.S. patent application Ser. No. 15/985,598, filed May 21, 2018, now U.S. Pat. No. 10,918, 778, which claims the benefit of priority of U.S. Provisional Application Ser. No. 62/510,652, filed May 24, 2017, the entire contents of each of which are incorporated herein by reference.

FIELD OF THE INVENTION

The present invention relates generally to improved systems and methods for conducting direct sodium removal via infusion and removal of a no or low sodium solution administered into a patient's peritoneal cavity to remove sodium and fluid from patients afflicted with heart failure or cardio-renal disease.

BACKGROUND

Patients afflicted with diverse forms of heart failure and/or cardio-renal disease are prone to the accumulation of additional sodium in body tissues and increased fluid retention. For example, in congestive heart failure, due to dysfunction of the left side or right side of the heart, or both, the body is unable to pump blood with normal efficiency, leading to the reduction of blood pressure in systemic circulation. In an attempt to increase blood pressure, the body retains sodium (and water), which leads to stasis or pooling of blood or fluid in the lungs or liver, edema and/or cardiac hypertrophy.

Methods, systems and compositions for directly removing excess sodium and water using a no or low sodium infusate instilled into a patient's peritoneal cavity are described in commonly-assigned U.S. Pat. No. 10,918,778, the entirety of which is hereby incorporated by reference. That patent describes a battery-powered pump, designed to be implanted subcutaneously, that includes an inlet catheter configured to be disposed within a patient's peritoneal cavity and an output catheter configured to be coupled to the patient's bladder. The pump is programmed to periodically actuate to move fluid from the peritoneal cavity to the bladder, where the fluid may be voided during urination.

As described in the above-incorporated patent, Direct Sodium Removal ("DSR") Therapy may be conducted periodically, e.g., daily or once weekly, to remove excess sodium and fluid from a patient to reduce fluid-overload, edema, and to reduce cardiac effort in patients with heart failure, such as Heart Failure with reduced Ejection Fraction ("HFrEF"). To conduct such therapy, a quantity, e.g., 0.5 to 1 liters, of a no or low sodium DSR solution is instilled into the patient's peritoneal cavity for a specified dwell period, such as two hours. Dwell time, however may be as long as 24 h, depending on type of DSR infusate used. During the dwell period, the DSR solution creates a sodium gradient that draws excess sodium from the patient's tissues and/or bloodstream into the peritoneal cavity, along with a corresponding volume of ultrafiltrate, e.g., water. At the conclusion of the dwell period, the implantable pump is actuated to move the now sodium-rich DSR solution and ultrafiltrate from the peritoneal cavity to the bladder. As observed in the above-incorporated patent and in initial human clinical testing, DSR therapy can reduce physiologically significant amounts of sodium and fluid from the patient, thereby reducing fluid overload and improving cardiac function.

One drawback of DSR therapy as described in the above patent is the use of a dwell period for the DSR solution in the patient's peritoneal cavity that is based on the physician's prior clinical experience and assessment of the patient's physiology. However, in view of the complexity and variability of human anatomy, it would be desirable to adapt the general DSR therapy to address the physiologic needs of specific patients. For example, some patients may have a high level of excess sodium stored in extravascular spaces, e.g., in interstitial spaces and tissues, whereas others may not. Consequently, using a predetermined dwell period for a DSR solution to remain in a patient's peritoneal cavity, e.g., 2 hours, may be suitable for one patient, too long for another, and too short for yet a different patient.

Accordingly, it would be desirable to equip the implantable pump used for DSR therapy with a feature that can assess the progress of the therapy, and actuate the pump to move the sodium rich DSR solution and ultrafiltrate to the patient's bladder after a predetermined goal or target is attained, independent of dwell time.

Further, it may be desirable to use conduct DSR therapy for a specific patient using DSR solutions having different compositions, e.g., concentrations of dextrose or dextrin, at different times. It therefore would be desirable to adapt the dwell time for DSR therapy to meet the specific physiologic needs and characteristics of a patient, as well as to account for different DSR solutions.

Accordingly, it would be desirable to develop systems and methods for conducting DSR therapy to remove sodium and fluid from a patient that permit titrating the treatment to the specific physiology of the patient and the DSR solution selected.

SUMMARY OF THE INVENTION

The present invention is directed to an implantable pump having features and programming adapted to conducting DSR therapy for patients suffering from fluid overload, e.g., heart failure patients and patients afflicted with cardio-renal disease. In accordance with one aspect of the invention, the implantable pump is configured having an inlet catheter designed for placement in a patient's peritoneal cavity, an outlet catheter designed to be coupled to the patient's bladder, an analyte sensing feature, and programming configured to actuate the pump responsive to the detected level of analyte.

In accordance with the principles of the present invention, the implantable pump may include, within the pump housing, associated with the inlet or outlet catheter, or as a separate lead disposed in the peritoneal cavity, a sensor for measuring a concentration of an analyte, such as sodium. In addition, the analyte sensor could also detect a concentration of an infusate component, such as dextrose or icodextrin, or an osmotic pressure or gradient, which could be used to determine when an infusate becomes hypotonic and should be drained from the peritoneal cavity. The detected analyte level is monitored by a processor and programming located within or in communication with the pump, and may be used to control actuation of the pump to move fluid from the peritoneal cavity to the patient's bladder when the detected analyte level meets a target level and/or to stop the pump to cease pumping. Additionally, the analyte may be monitored continuously during pumping so that, in conjunction with the volume of fluid removed during a pump session recorded by the pump controller, an estimate of the amount of sodium removed during a specified pumping session or interval may be computed and reported to the patient and/or the patient's caretaker or physician. As a further alternative, the monitored analyte value may be transmitted to the patient, his or her caretaker or physician, who may issue commands to control actuation of the implantable pump.

More particularly, in the context of DSR therapy, a quantity of DSR solution is instilled into the peritoneal cavity of a patient suffering from fluid overload. As described in the above-incorporated patent, because the no or low sodium DSR solution creates a gradient, it draws excess sodium and fluid from the patient's tissue into the peritoneal cavity through one or both of ultrafiltration and/or diffusion down a steep concentration gradient. In contrast to previously known methods of conducting DSR therapy, rather than waiting for a predetermined dwell period to elapse, the implantable pump may be configured to monitor the sodium concentration in the peritoneal cavity via the sensor, or to monitor the total amount of sodium transferred with fluid moved to the patient's bladder. When the sodium concentration in the peritoneal cavity reaches a target level, e.g., determined by the clinician and implemented in the pump programming, the processor actuates the pump to move the now sodium rich DSR solution and ultrafiltrate from the peritoneal cavity to the bladder, where it is voided during urination. Preferably, the target sodium concentration that triggers pump actuation is selected to eliminate excess sodium and fluid from the body while maintaining a stable serum sodium concentration. In this manner, the inventive pump reduces hypervolemia while avoiding hyponatremia. In addition, because in a preferred embodiment the pump employs a positive displacement gear pump, the precise volume of fluid moved to the patient's bladder during a pumping session may be used, together with the analyte concentration, to estimate a value of the total amount of sodium removed during a specific pumping session, and/or to cease pumping fluid from the peritoneal cavity to the bladder. This information also may be useful, for example, in determining the timing for a subsequent DSR treatment and/or to adjust the volume of DSR solution required for a subsequent treatment.

In accordance with another aspect of the invention, the processor also may be programmed to actuate the pump to move the DSR solution, sodium and ultrafiltrate from the peritoneal cavity to the bladder after expiration of a predetermined dwell time. Such programming may serve as a fail-safe in the event that monitored sodium concentration level in the patient's peritoneal cavity does not meet the predetermined target level, or if a fault arises in the analyte sensor or monitoring programming.

The implantable pump further may include programming that tracks the monitored analyte level to ensure completion of removal of the DSR solution and ultrafiltrate once the target analyte level is reached for a DSR therapy session. For example, if all fluid in the peritoneal cavity is not pumped to the bladder during a first pump actuation period, e.g., to give the pump motor a rest period or because the bladder is full, the pump is configured to monitor the pressure in the peritoneal cavity and resume moving fluid once the rest period ends or the bladder is voided. In this way, the system ensures that the analyte monitoring system cannot dither as sodium concentration decreases during pump activation, and ensures that each separate DSR therapy session concludes.

Further, because in a preferred embodiment the implantable pump uses a positive displacement gear pump to move fluid, the total amount of analyte may be computed for each pumping session as the concentration multiplied by the volume of fluid transiting the pump.

The system and methods of the present invention are expected to greatly increase patient comfort during DSR therapy sessions, as well as patient safety. For example, if the analyte sensor detects that the targeted sodium level is attained prior to the expiration of a dwell period based on time alone, the implantable pump can complete the DSR therapy session sooner for a particular patient, thereby enhancing the patient's quality of life. In addition, by completing the session sooner than might be determined by awaiting expiration of a predetermined time period, the inventive system ensures that hyponatremia is avoided. Moreover, because the inventive system and methods respond to the detected analyte concentration, they should provide an additional level safety when the composition of the DSR solution is changed.

Other features of the inventive system and methods will be apparent with reference to the following description and figures.

BRIEF DESCRIPTION OF THE DRAWINGS

FIG. 3 is a schematic diagram of the electronic components of an exemplary embodiment of the implantable device.

FIGS. 4A and 4B are, respectively, a perspective view of the implantable device with the housing shown in outline and a perspective view of the obverse side of the implantable device with the housing and low water permeable filler removed.

FIG. 12 illustrates steps of an exemplary method in accordance with the principles of the present invention using the system of FIG. 1.

DETAILED DESCRIPTION OF THE INVENTION

Figure 1:
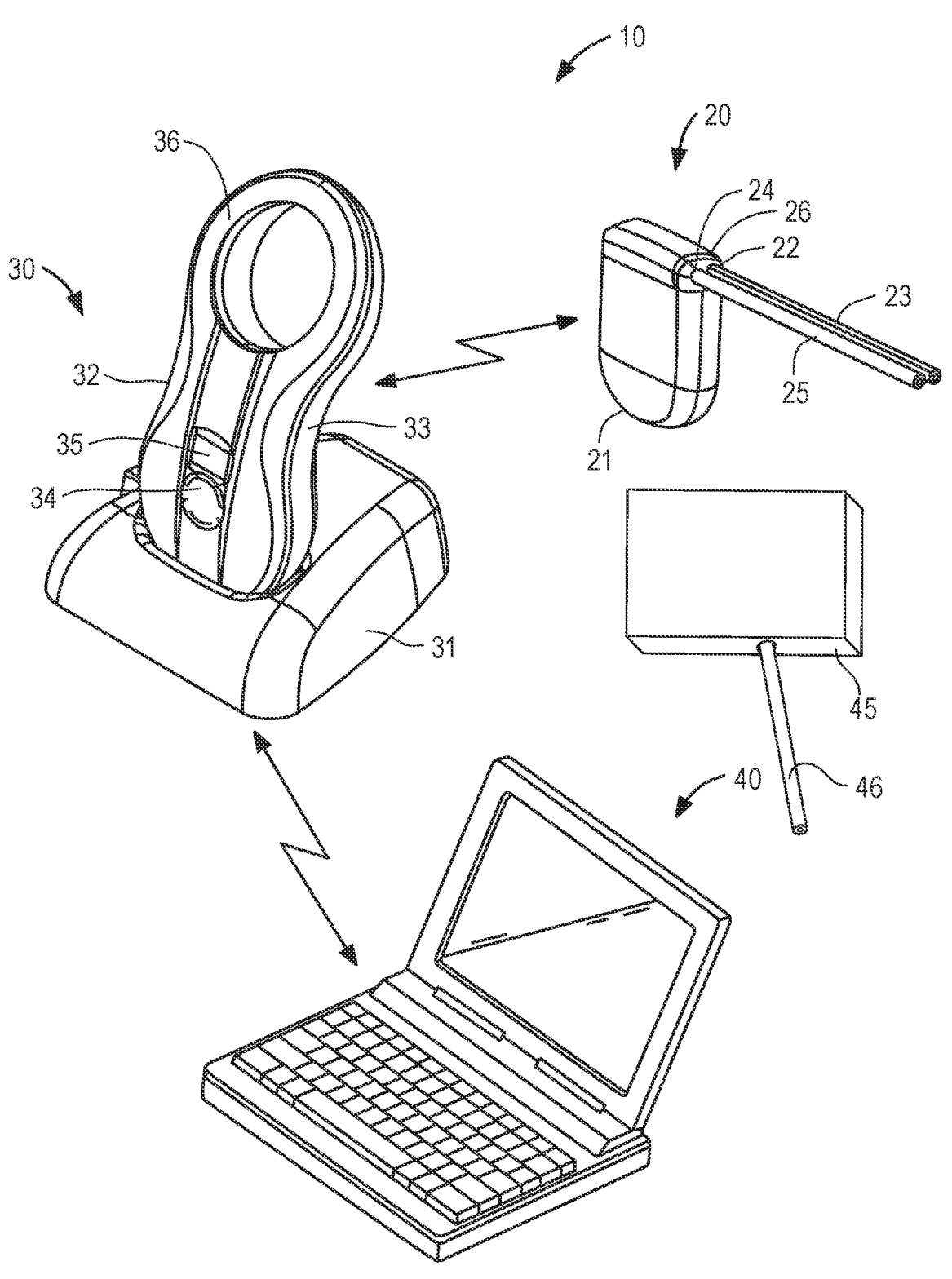
FIG. 1 is a perspective view of an exemplary system constructed in accordance with the principles of the present invention for use in performing DSR therapy.

The present invention is directed to system and methods for conducting direct sodium removal ("DSR") therapy using compositions as described in above-incorporated U.S. Pat. No. 10,918,778. As described in that patent, DSR therapy may be used to treat fluid overload in various forms of heart failure, such as left heart or right heart dysfunction. In accordance with the principles of the present invention, improved systems and methods are provided for conducting DSR therapy in which an analyte sensor associated with an implantable pump is used to monitor an analyte concentration in the fluid in the peritoneal cavity and/or an amount of analyte removed by the implantable pump during a pumping session. Once the analyte concentration attains a target value programmed for that DSR therapy session, or a maximum dwell time is reached, the pump is actuated to move sodium-laden DSR solution and ultrafiltrate from the peritoneal cavity to the patient's bladder. The output of the analyte sensor also may be used by the pump controller, together with the volume of fluid transferred to the bladder by the implantable pump, to determine an estimate of the volume of analyte removed from the peritoneal cavity to the bladder. In addition, the analyte sensor may be configured to measure a concentration of one or more components of the DSR fluid, e.g., dextrose or icodextrin concentration, to adjust the dwell time for the DSR therapy session.

As described in the above-incorporate patent, the no or low sodium concentration in the DSR solution causes sodium and fluid (osmotic ultrafiltrate) to pass from the patient's body into the peritoneal cavity. As used in this disclosure, a no or low sodium DSR solution has a sodium content of less than 120 meq/L, more preferably, less than 35 meq/L, and includes infusates having virtually zero concentration of sodium. Accordingly, the methods of the present invention specifically contemplate use of the inventive system to monitor the present of an analyte in the fluid accumulated in the peritoneal cavity, preferably sodium, and to trigger actuation of the pump to move the DSR solution/ultrafiltrate to the patient's bladder. That fluid then is voided via urination.

Exemplary DSR solution formulations presented in the incorporated patent include D-0.5 to D-50 solutions, i.e., from 0.5 to 50 grams of dextrose per 100 ml of aqueous solution; Icodextrin or dextrin solutions having from 0.5 to 50 grams of icodextrin/dextrin per 100 ml of aqueous solution; urea, and high molecular weight glucose polymer solutions (weight average molecular weight Da>10,000) having from 0.5 to 50 grams of high molecular weight glucose polymer per 100 ml of aqueous solution, and combinations thereof. The aqueous solution includes at least purified water, and may in addition include electrolytes such as low amounts of magnesium or calcium salts, preservatives, ingredients having antimicrobial or antifungal properties, or buffering materials to control pH of the infusate. Icodextrin, a high molecular weight glucose polymer, or other high molecular weight glucose polymer (weight average molecular weight, Da>10,000,) is preferable because it experiences a lower rate of uptake when employed in peritoneal dialysis, and thus lower impact on serum glucose concentrations compared to a dextrose-based solutions.

Overview of an Exemplary System of the Present Invention

Referring to FIG. 1, exemplary system 10 of the present invention is described. In FIG. 1, components of the system are not depicted to scale on either a relative or absolute basis. System 10 comprises implantable device 20, external charging and communication system 30, software-based monitoring and control system 40, and optionally, reservoir 45. In the illustrated embodiment, monitoring and control system 40 is configured to be installed and run on a conventional laptop computer, tablet or smartphone, as may be used by the patient's physician. During patient visits, charging and communication system 30 may be coupled, either wirelessly or using a cable, to monitoring and control system 40 to download for review data stored on implantable device 20, or to adjust the operational parameters of the implantable device. Monitoring and control system 40 also may be configured to upload and store date retrieved from charging and communication system 30 to a remote server for later access by the physician or charging and communications system 30.

Implantable device 20 comprises an electromechanical pump having housing 21 configured for subcutaneous implantation. Implantable device 20 may include an electrically-driven mechanical gear pump and connectors 22 and 24 configured to reduce the risk of improper installation and inadvertent disconnection. Bladder catheter 25 is coupled to pump housing 21 using connector 24. Peritoneal catheter 23 is coupled to pump housing 21 using connector 22. Peritoneal catheter 23 has a proximal end configured to be coupled to pump housing 21 and a distal end configured to be positioned in the peritoneal cavity. Bladder catheter 25 has a proximal end configured to be coupled to pump housing 21 and a distal end configured to be inserted through the wall of, and fixed within, a patient's bladder. In a preferred embodiment, both catheters are made of medical-grade silicone and include polyester cuffs at their distal ends (not shown) to maintain the catheters in position.

In a preferred embodiment, implantable device 20 includes pressure sensors that monitor pressure in one or both of the peritoneal cavity and the bladder. Implantable device 20 also preferably includes at least one analyte sensor for generating an output signal corresponding to concentration of a predetermined analyte, such as sodium, or a concentration of an infusate component, such as dextrose or icodextrin. In this manner, movement of sodium-laden DSR solution and ultrafiltrate fluid from the peritoneal cavity to the bladder may be controlled in accordance with one or more target analyte concentrations determined by the physician. In addition, the output of the pressure sensors may cause pumping of fluid into the bladder to be disabled if the bladder pressure reaches a level indicating insufficient space for the bladder to accommodate additional fluid or if the pressure in the peritoneal cavity falls below preset threshold. For patient comfort, implantable device 20 optionally may be programmed not to pump at night or when an accelerometer included in the implantable device indicates that the patient is asleep (and thus unlikely to be able to void the bladder). Implantable device 20 preferably includes multiple separate fail-safe mechanisms, to ensure that urine cannot pass from the bladder to the peritoneal cavity through the pump, thereby reducing the risk of transmitting infection.

On/off operation of implantable device so also may be actuated responsive to the additional analyte sensors, if present.

Still referring to FIG. 1, external charging and communication system 30 of the exemplary system, preferably includes base 31 and handpiece 32. Handpiece 32 may contain a controller, a radio transceiver, an inductive charging circuit, a battery, a quality-of-charging indicator and a display, and may be removably coupled to base 31 to recharge the battery. Base 31 may contain a transformer and circuitry for converting conventional 120V or 220-240V service to a suitable DC current to charge handpiece 32 when coupled to base 31. Alternatively, handpiece 32 may include such circuitry and a detachable power cord, thus permitting the handpiece to be directly plugged into a wall socket to charge the battery. Preferably, each of implantable device 20 and handpiece 32 includes a device identifier stored in memory, such that handpiece 32 provided to the patient is coded to operate only with that patient's specific implantable device 20.

Handpiece 32 illustratively includes housing 33 having multi-function button 34, display 35, a plurality of light emitting diodes (LEDs, not shown) and inductive coil portion 36. Multi-function button 34 enables the patient to issue a limited number of commands to implantable device 20, while display 35 provides visible confirmation that a desired command has been input; it also may display battery status of implantable device 20. Inductive coil portion 36 houses an inductive coil that is used transfer energy from handpiece 32 to recharge the battery of implantable device 20. The LEDs, which are visible through the material of housing 33 when lit, may be arranged in three rows of two LEDs each, and are coupled to the control circuitry and inductive charging circuit contained within handpiece 32. The LEDs may be arranged to light up to reflect the degree of inductive coupling achieved between handpiece 32 and implantable device 20 during recharging of the latter. Alternatively, the LEDs may be omitted and an analog display provided on display 35 indicating the quality of inductive coupling.

Control circuitry contained within handpiece 32 is coupled to the inductive charging circuit, battery, LEDs and radio transceiver, and includes memory for storing information received from implantable device 20. Handpiece 32 also preferably includes a data port, such as a USB port, that permits the handpiece to be coupled to monitoring and control system 40 during visits by the patient to the physician's office. Alternatively, handpiece 32 may include a wireless chip, e.g., that conforms to the Bluetooth or IEEE 802.11 wireless standards, thereby enabling the handpiece to communicate wirelessly with monitoring and control system 40, either directly or via the Internet.

Monitoring and control system 40 is intended primarily for use by the physician and comprises software configured to run on a conventional computer, e.g., a laptop as illustrated in FIG. 1, or a tablet or smartphone. The software enables the physician to configure, monitor and control operation of charging and communication system 30 and implantable device 20. The software may include routines for configuring and controlling pump operation, such as a target analyte concentration at which pumping is actuated, the amount of analyte transferred from the peritoneal cavity to the bladder during a pumping session, a maximum dwell time for the DSR therapy, and limits on maximum and minimum peritoneal cavity pressure, bladder pressure, pump pressure, and battery temperature. System 40 also may provide instructions to implantable device 20 via charging and control system 30 to control operation of implantable device 20 so as not to move fluid during specific periods (e.g., at night or when the bladder is full) or to defer pump actuation.

System 40 also may be configured, for example, to send immediate commands to the implantable device to start or stop the pump, or to operate the pump in reverse or at high power to unblock the pump or associated catheters. The software of system 40 may be configured to download real-time data relating to pump operation, as well as event logs stored during operation of implantable device 20. Based on the downloaded data, e.g., based on measurements made of the patient's analyte concentration, intra-abdominal pressure, respiratory rate, and/or fluid accumulation, the software of system 40 optionally may be configured to alert the physician. Such alerts may include to a prediction or detection of heart failure decompensation or a change in the patient's health for which an adjustment to the flow rate, volume, time and/or frequency of pump operation may be required. Finally, system 40 optionally may be configured to remotely receive raw or filtered operational data from handpiece 32 over a secure Internet channel.

Figure 2A:
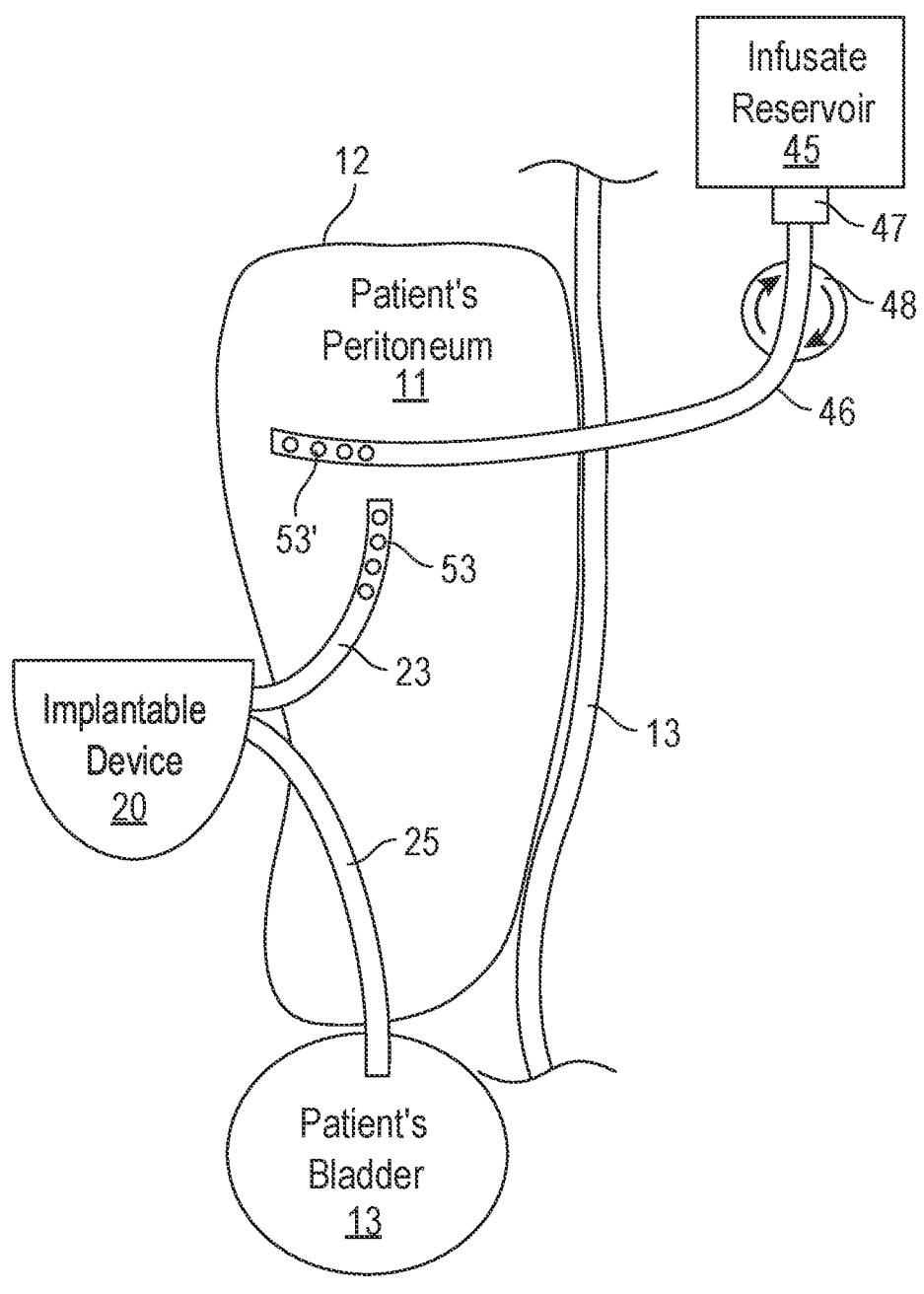
FIG. 2A is a plan view of selected components of the system of FIG. 1 as implanted in a patient.
Figure 2B:
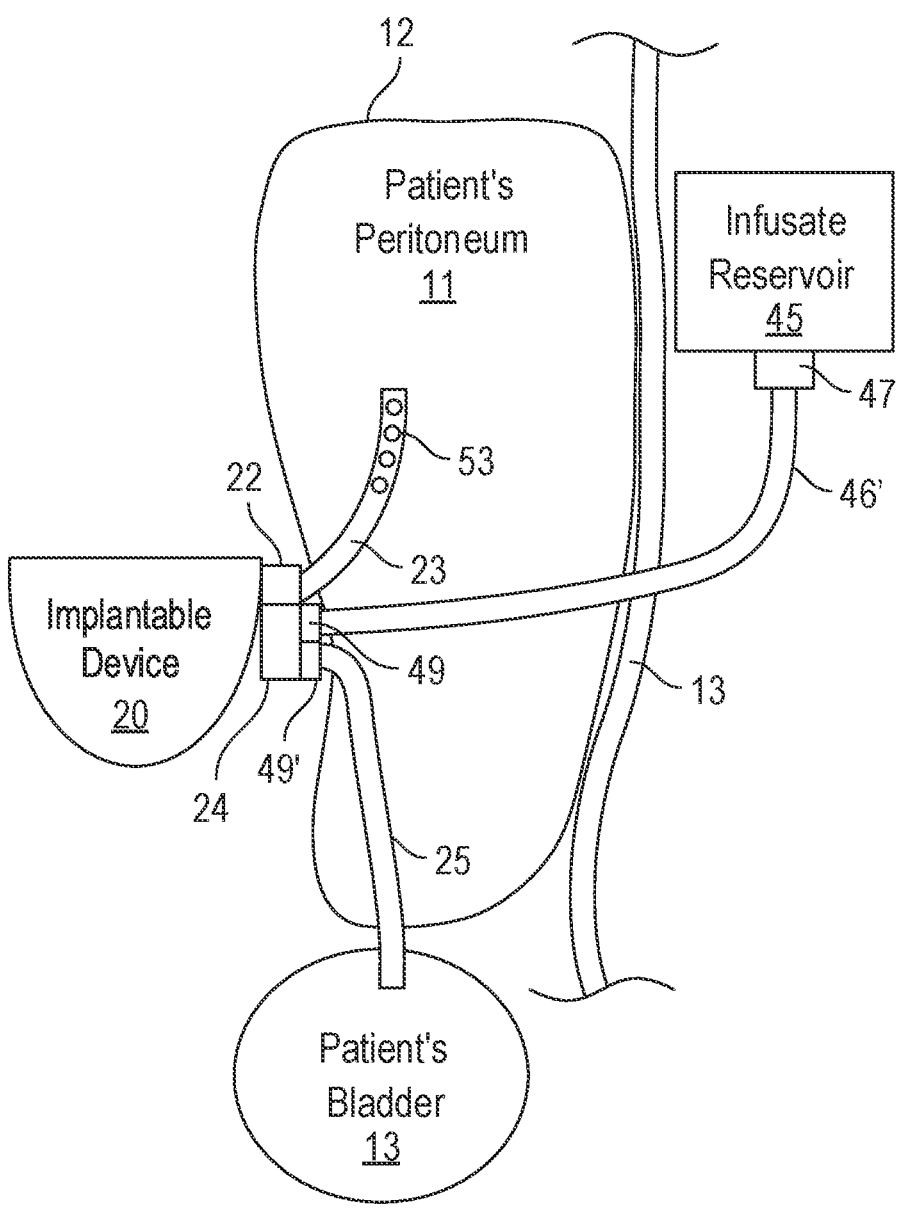
FIG. 2B is a plan view of selected components of an alternative embodiment of an exemplary system for practicing the methods of the present invention.

Turning now to FIGS. 2A and 2B, alternative configurations of implantable device 20 and optional DSR solution reservoir 45 are described.

In FIG. 2A, an exemplary use of implantable device 20 for implementing the methods of the present invention is described. Device 20 is implanted subcutaneously, preferably outside of the patient's peritoneal cavity 11 as defined by peritoneal membrane 12. Implantable device 20 is placed beneath skin 13 so that the device may readily be charged by, and communicate with, charging and communication system 30. Device 20 is coupled via appropriate connectors (not shown) to peritoneal catheter 23 and bladder catheter 25. Peritoneal catheter 23 is configured for implantation in the patient's peritoneal cavity 11 and preferably includes apertures 53 described further detail below that permit fluid to be suctioned to device 20. Bladder catheter 25 is configured for implantation in the patient's bladder 13 and preferably includes an anchor that secures the outlet end of the catheter within the bladder 13, such as further described below.

Optional DSR solution reservoir 45, which may consist of a sterile bag, is positioned outside of the body and has an outlet of catheter 46 disposed in the peritoneal cavity. Catheter 46 is coupled to reservoir 45 via connector 47 and preferably includes apertures 53' that allow the DSR solution to flow into the peritoneal cavity 11 in a relatively diffuse manner. Optional external pump 48 may be configured to move DSR solution from reservoir 45 into the peritoneal cavity 11 at a desired rate. For example, reservoir 45 may be positioned on a belt (not shown) that is worn around the patient's waist and includes pump 48. Pump 48 may be configured to communicate wirelessly with implantable device 20 so as to coordinate delivery of DSR solution into the patient's peritoneal cavity. Alternatively, reservoir 45 may be positioned at a level above peritoneal cavity 11 such that gravity causes the DSR solution to flow from reservoir 45 into the peritoneum at a desired rate.

Referring to FIG. 2B, an alternative embodiment in which reservoir 45 is positioned outside of the patient's body, e.g., using a belt or harness, and coupled to implantable device 20 via catheter 46' and connector 47 us described. In this embodiment, implantable device 20 is configured to transfer DSR solution into peritoneal cavity 11 from reservoir 45 via catheters 46' and 23. At a later time, e.g., when triggered by the detected sodium concentration in the peritoneal cavity exceeding a target level, device 20 moves the sodium-laden DSR solution and osmotic ultrafiltrate from peritoneal cavity 11 into bladder 13 via catheters 23 and 25.

More specifically, in the embodiment of FIG. 2B, connector 24 of implantable device 20 comprises first valve 49' to which catheter 25 is connected and second valve 49 to which catheter 46' is connected. Connector 22 of implantable device 20 is directly connected to catheter 23. During pumping operations, implantable device 20 controls valves 49 and 49' so as to prevent fluid from being inadvertently transferred from the bladder into the peritoneal cavity or from the peritoneal cavity into the reservoir. For example, to transfer fluid into peritoneal cavity 11 from reservoir 45, implantable device 20 may close fluidic communication to catheter 25 by appropriately actuating valve 49', open fluidic communication between catheters 46' and 23 by appropriately actuating valve 49, and move fluid from reservoir 45 via catheters 46' and 23. Reservoir 45 may alternatively be implanted inside the patient's body and connected to the exterior environment using a catheter or subcutaneous port and needle to permit reservoir 45 to be refilled.

After the analyte concentration of the fluid in the peritoneal cavity reaches a predetermined target value, or if a maximum dwell is reached without attaining the target level, implantable device 20 is actuated to move sodium laden DSR solution and accumulated osmotic ultrafiltrate from the peritoneal cavity to patient bladder 13. This is accomplished by closing communication to catheter 46' by actuating valve 49, opening communication to catheter 25 by actuating valve 49', and transferring fluid into bladder 13 via catheters 23 and 25. It should be appreciated that the functionalities of valves 49 and 49' may be provided by any desired number of valves disposed appropriately along catheters 23, 25, and 46', which are controllably actuated by implantable device 20. In certain configurations, the use of one or more passive valves (not controlled by implantable device 20) may be used, e.g., valve 49' may be a passive check valve disposed along catheter 25 that inhibits fluid to flow from the bladder to device 20.

Further details of selected components of the inventive system of FIG. 1 and methods are now provided with reference to FIGS. 3 through 12.

The Implantable Device

Referring now to FIG. 3, a schematic depicting the functional blocks of implantable device 20 suitable for use in practicing the methods of the present invention is described. Implantable device 20 includes control circuitry, illustratively processor 70 coupled to nonvolatile memory 71, such as flash memory or electrically erasable programmable read only memory, and volatile memory 72 via data buses. Processor 70 is electrically coupled to electric motor 73, battery 74, inductive circuit 75, radio transceiver 76, one or more analyte sensors 85, and a plurality of other sensors, including humidity sensor 77, one or more temperature sensors 78, accelerometer 79, pressure sensors 80, and respiratory rate sensor 81. Inductive circuit 75 is electrically coupled to coil 84 to receive energy transmitted from charging and communication system 30, while transceiver 76 is coupled to antenna 82, and likewise is configured to communicate with a transceiver in charging and communication system 30, as described below. Optionally, inductive circuit 75 also may be coupled to infrared light emitting diode 83. Motor 73 may include a dedicated controller, which interprets and actuates motor 73 responsive to commands from processor 70. Optionally, processor 70 is further in communication with valve controller 86. All of the components depicted in FIG. 3 are contained within a low volume sealed biocompatible housing, depicted in FIG. 4A.

Processor 70 executes firmware stored in nonvolatile memory 71 which controls operation of motor 73 responsive to signals generated by motor 73, sensors 77-81 and 85, and commands received from transceiver 76. Processor 70 also controls reception and transmission of messages via transceiver 76 and operation of inductive circuit 75 to charge battery 74. In addition, processor 70 receives signals generated by Hall Effect sensors located within motor 73, which are used to compute direction and revolutions of the gears of the gear pump, and thus fluid volume transferred and the viscosity of that fluid, as described below. Processor 70 preferably includes a low-power mode of operation and includes an internal clock, such that the processor can be periodically awakened to handle pumping, pump tick mode, or communications and charging functions, and/or awakened to handle commands received by transceiver 76 from handpiece 32. In one embodiment, processor 70 comprises a member of the MSP430 family of microcontroller units available from Texas Instruments, Incorporated, Dallas, Tex., and may incorporate the nonvolatile memory, volatile memory, and radio transceiver components depicted in FIG. 3. In addition, the firmware executed on processor 70 may be configured to respond directly to commands sent to implantable device 20 via charging and communication system 30. Processor 70 also is configured to monitor operation of motor 72 (and any associated motor controller) and sensors 77-81 and 85, as described below, and to store data reflecting operation of the implantable device, including event logs and alarms. Such stored data may be reported to the charging and communication system when it is next wirelessly coupled to the implantable device. In a preferred embodiment, processor 70 generates up to eighty log entries per second prior to activating the pump, about eight log entries per second when the implantable system is actively transferring fluid and about one log entry per hour when not transferring fluid.

Nonvolatile memory 71 preferably comprises flash memory or EEPROM, and stores a unique device identifier for implantable device 20, firmware to be executed on processor 70, configuration set point data relating to operation of the implantable device, and optionally, coding to be executed on transceiver 76 and/or inductive circuit 75, and a separate motor controller, if present. Firmware and set point data stored on nonvolatile memory 71 may be updated using new instructions provided by control and monitoring system 40 via charging and communication system 30. Volatile memory 72 is coupled to and supports operation of processor 70, and stores data and event log information gathered during operation of implantable device 20. Volatile memory 72 also serves as a buffer for communications sent to, and received from, charging and communication system 30.

Transceiver 76 preferably comprises a radio frequency transceiver and is configured for bi-directional communications via antenna 76 with a similar transceiver circuit disposed in handpiece 32 of charging and communication system 30. Transceiver 76 also may include a low power mode of operation, such that it periodically awakens to listen for incoming messages and responds only to those messages that include the unique device identifier assigned to that implantable device. Alternatively, because transceiver 76 communicates only with the corresponding transceiver in handpiece 32 of its associated charging and communication system 30, transceiver 76 may be configured to send or receive data only when inductive circuit 75 of the implantable device is active. Transceiver 76 may employ an encryption routine to ensure that messages sent from, or received by, the implantable device cannot be intercepted or forged.

Inductive circuit 75 is coupled to coil 84, and is configured to recharge battery 74 of the implantable device when exposed to a magnetic field applied by a corresponding inductive circuit within handpiece 32 of charging and communication system 30. In one embodiment, inductive circuit 75 is coupled to optional infrared LED 83 that emits an infrared signal when inductive circuit 75 is active. The infrared signal may be received by handpiece 32 to assist in locating the handpiece relative to the implantable device, thereby improving the magnetic coupling and energy transmission.

Inductive circuit 75 optionally may be configured not only to recharge battery 74, but to directly provide energy to motor 73 in a "boost" mode or jog/shake mode to unblock the pump. In particular, if processor 70 detects that motor 73 is stalled, e.g., due to a block created by fibrin or other debris in the peritoneal cavity, an alarm may be stored in memory. When implantable device 20 next communicates with charging and communication system 30, the alarm is reported to handpiece 32, and the patient may be given the option of depressing multifunction button 34 to apply an overvoltage to motor 73 from inductive circuit 75 for a predetermined time period to free the pump blockage. Alternatively, depressing the multi-function button may cause processor 70 to execute a set of commands by which motor 73 is jogged or shaken, e.g., by alternatingly running the motor in reverse and then forward, to disrupt the blockage. Because such modes of operation may employ higher energy consumption than expected during normal operation, it is advantageous to drive the motor during such procedures with energy supplied via inductive circuit 75.

Battery 74 preferably comprises a lithium ion or lithium polymer battery capable of long lasting operation, e.g., up to three years, when implanted in a human, so as to minimize the need for re-operations to replace implantable device 20. In one preferred embodiment, battery 74 supplies a nominal voltage of 3.6V, a capacity of 150 mAh when new, and a capacity of about 120 mAh after two years of use. Preferably, battery 74 is configured to supply a current of 280 mA to motor 73 when pumping; 25 mA when the transceiver is communicating with charging and communication system 30; 8 mA when processor 70 and related circuitry is active, but not pumping or communicating; and 0.3 mA when the implantable device is in low power mode. More preferably, battery 74 should be sized to permit a minimum current of at least 450 mAh for a period of 10 seconds and 1 A for 25 milliseconds during each charging cycle.

Motor 73 preferably is a brushless direct current or electronically commuted motor having a splined output shaft that drives a set of floating gears that operate as a gear pump, as described below. Motor 73 may include a dedicated motor controller, separate from processor 70, for controlling operation of the motor. Motor 73 may include a plurality of Hall Effect sensors, preferably two or more, for determining motor position and direction of rotation. Due to the high humidity that may be encountered in implantable device 20, processor 70 may include programming to operate motor 73, although with reduced accuracy, even if some or all of the Hall Effect sensors fail.

In a preferred embodiment, motor 73 is capable of driving the gear pump to generate a nominal flow rate of 150 ml/min and applying a torque of about 1 mNm against a pressure head of 30 cm water at 3000 RPM. In this embodiment, the motor preferably is selected to drive the gears at from 1000 to 5000 RPM, corresponding to flow rates of from 50 to 260 ml/min, respectively. The motor preferably has a stall torque of at least 3 mNm at 500 mA at 3 V, and more preferably 6 mNm in order to crush non-solid proteinaceous materials. As discussed above, the motor preferably also supports a boost mode of operation, e.g., at 5 V, when powered directly through inductive circuit 75. Motor 73 preferably also is capable of being driven in reverse as part of a jogging or shaking procedure to unblock the gear pump.

Processor 70 also may be programmed to automatically and periodically wake up and enter a pump tick mode. In this mode of operation, the gear pump is advanced slightly, e.g., about 120 degrees as measured by the Hall Effect sensors, before processor 70 returns to low power mode. Preferably, this interval is about every 20 minutes, although it may be adjusted by the physician using the monitoring and control system. Tick mode is expected to prevent the DSR solution and ultrafiltrate from partially solidifying and blocking the gear pump.

Processor 70 also may be programmed to enter a jog or shake mode when operating on battery power alone, to unblock the gear pump. Similar to the boost mode available when charging the implantable device with the handpiece of charging and communication system 30, the jog or shake mode causes the motor to rapidly alternate the gears between forward and reverse directions to crush or loosen any buildup of tissue or other debris in the gear pump or elsewhere in the fluid path. Specifically, in this mode of operation, if the motor does not start to turn within a certain time period after it is energized (e.g., 1 second), the direction of the motion is reversed for a short period of time and then reversed again to let the motor turn in the desired direction. If the motor does still not turn (e.g., because the gear pump is jammed) the direction is again reversed for a period of time (e.g., another 10 msec). If the motor still is unable to advance, the time interval between reversals of the motor direction is reduced to allow the motor to develop more power, resulting in a shaking motion of the gears. If the motor does not turn forward for more than 4 seconds, the jog mode of operation ceases, and an alarm is written to the event log. If the motor was unable to turn forward, processor 70 may introduce a backwards tick before the next scheduled fluid movement. A backward tick is the same as a tick (e.g., about 120 degrees forward movement of the motor shaft) but in a reverse direction, and is intended to force the motor backwards before turning forward, thus allowing the motor to gain momentum.

Sensors 77-81 continually monitor humidity, temperature, acceleration, pressure, and respiratory rate, and provide corresponding signals to processor 70 which stores the corresponding data in memory 71 for later transmission to monitoring and control system 40. In particular, humidity sensor 77 is arranged to measure humidity within the housing of the implantable device, to ensure that the components of implantable device are operated within expected operational limits. Humidity sensor 77 preferably is capable of sensing and reporting humidity within a range or 20% to 100% with high accuracy. One or more of temperature sensors 78 may be disposed within the housing and monitor the temperature of the implantable device, and in particular battery 74 to ensure that the battery does not overheat during charging, while another one or more of temperature sensors 78 may be disposed so as to contact fluid entering at inlet 62 and thus monitor the temperature of the fluid, e.g., for use in assessing the patient's health. Accelerometer 79 is arranged to measure acceleration of the implant, preferably along at least two axes, to detect periods of activity and inactivity, e.g., to determine whether the patient is sleeping or to determine whether and when the patient is active. This information is provided to processor 70 to ensure that the pump is not operated when the patient is indisposed to attend to voiding of the bladder.

Implantable device 20 preferably includes multiple pressure sensors 80, which are continually monitored during waking periods of the processor. As described below with respect to FIG. 5A, the implantable device preferably includes four pressure sensors: a sensor to measure the pressure in the peritoneal cavity, a sensor to measure the ambient pressure, a sensor to measure the pressure at the outlet of the gear pump, and a sensor to measure the pressure in the bladder. These sensors preferably are configured to measure absolute pressure between 450 mBar and 1300 mBar while consuming less than 50 mW at 3V. Preferably, the sensors that measure pressure at the pump outlet and in the bladder are placed across a duckbill valve, which prevents reverse flow of urine and/or used DSR solution and ultrafiltrate back into the gear pump and also permits computation of flow rate based on the pressure drop across the duckbill valve.

Respiratory rate monitor 81 is configured to measure the patient's respiratory rate, e.g., for use in assessing the patient's health. Alternatively, the patient's respiratory rate may be measured based on the outputs of one or more of pressure sensors 80, e.g., based on changes in the ambient pressure or the pressure in the peritoneal cavity caused by the diaphragm periodically compressing that cavity during breathing.

In accordance with one aspect of the present invention, analyte sensor 85 may be a chemical or biochemical sensor configured to monitor a sodium concentration of sodium-laden DSR solution and ultrafiltrate instilled into and accumulated within the patient's peritoneal cavity. Analyte sensor 85 may in addition sense a concentration of a component, such as dextrose or icodextrin concentration, in the DSR solution present in the peritoneal cavity, and that information may be used by the processor of implantable device 20 to trigger starting or stopping of the pump. One exemplary in vivo sensor suitable for monitoring sodium ion concentration is described in U.S. Patent Application Publication No. 2008/033260, the entirety of which is incorporated herein by reference. Analyte sensor 85 may be disposed on catheter 23, on catheter 25, or may be disposed within the housing of implantable device 20 so as to contact fluid flowing through the device. Any desired number of additional sensors for measuring the health of the patient also may be provided in operable communication with processor 70 and may output recordable parameters for storage in memory 71 and transmission to monitoring and control system 40, that the physician may use to assess the patient's health.

In an exemplary embodiment, processor 70 may be programmed to monitor an output of analyte sensor 85, for example, indicative of a value of sodium concentration, and to compare that value to a target sodium concentration value selected by the physician at which implantable device 20 is activated to transfer fluid from the peritoneal cavity to the patient's bladder. Alternatively, or in addition, analyte sensor 85 could measure a concentration of an infusate component remaining in the peritoneal cavity. Processor 70 also may be programmed to activate implantable device 20 to move fluid from the peritoneal cavity to the bladder after that fluid has dwelled in the peritoneal cavity a sufficient period that the measured analyte concentration exceeds or falls below a target value. In addition, fluid transfer may be initiated after infusate has dwelled in the peritoneal cavity for a predetermined maximal amount of time, which may be set by a physician. For this purpose, processor 70 may include a programmed timer that monitors the dwell time, e.g., elapsed time from when the DSR solution is first introduced into the patient's peritoneal cavity. As a further alternative, processor 70 may be programmed to compute an estimate of the amount of analyte transferred from the peritoneal cavity to the bladder as function of the measured concentration and the volume of fluid transferred, and to report that amount to the patient, physician or caretaker. Such information may, in turn, be used to determine when the next DSR therapy session should occur or be used in adjusting the volume of DSR solution to be employed during a subsequent DSR therapy session.

The volume of fluid transferred, and pump activation time and frequency may be selected to optimize sodium removal to maintain or improve the patient's health, to alleviate the fluid overload and to ensure a stable serum sodium level. These parameters may be selected based on the patient's symptoms, the activity and habits of the patient, the permeability of the peritoneal membrane and the osmotic characteristics of the DSR solution, and they may be static or changed by the physician on a session-by-session basis. For example, the physician may initially program processor 70 with a first sodium concentration level, amount of sodium to be removed, maximum dwell time, volume, or frequency based on his perception of the patient's health and habits, and later adjust that initial programming to vary those parameters based on his perception of changes in the patient's health, for example based on changes over time in parameters measured by implantable device 20 and relayed to the physician via monitoring and control software 40.

Processor 70 also may be programmed to monitor the sensors 77-81 and to generate an alert condition that is relayed to the clinician indicative of a potential decline in the patient's health. For example, processor 70 may monitor pressure sensors 80 to determine whether, over predetermined time intervals, there is an increase in pressure within the peritoneal cavity. Such pressure increases may be the result of an increase in the rate of accumulation of fluid in the peritoneal cavity, which may in turn indicate heart failure decompensation. Such an alert may result in the patient being directed to seek immediate treatment.

Processor 70 further may be programmed to pump fluid from the peritoneal cavity to the bladder only when the pressure in the peritoneal cavity exceeds a first predetermined value, and the pressure in the bladder is less than a second predetermined value, so that the bladder does not become overfull. To account for patient travel from a location at sea level to a higher altitude, the ambient pressure measurement may be used to calculate a differential value for the peritoneal pressure. In this way, the predetermined pressure at which the pump begins operation may be reduced, to account for lower atmospheric pressure. Likewise, the ambient pressure may be used to adjust the predetermined value for bladder pressure. In this way, the threshold pressure at which the pumping ceases may be reduced, because the patient may experience discomfort at a lower bladder pressure when at a high altitude location.

Further, processor 70 may be programmed to permit transfer of fluid from the peritoneal cavity to the bladder to be interrupted, for example if the bladder pressure indicates that the bladder is full, and to resume transferring fluid once the bladder pressure sensor detects that the bladder has been voided. In this case, because the sodium concentration level may have fallen due to fluid transfer immediately before the bladder was detected to be full, the process may be programmed to resume fluid transfer once the sodium concentration level has reached the target level during a single DSR therapy session.

Optionally, implantable device 20 may include a UV lamp (not shown) disposed in operable communication with controller 70. The UV lamp may be configured to irradiate and thus kill pathogens in the DSR solution before is instilled into and/or after fluid is extracted from the peritoneal cavity. The UV lamp preferably generates light in the UV-C spectral range (about 200-280 nm), particularly in the range of about 250-265 nm, which is also referred to as the "germicidal spectrum" because light in that spectral range breaks down nucleic acids in the DNA of microorganisms. Low-pressure mercury lamps have an emission peak at approximately 253.7 nm, and may suitably be used for UV lamp 85. Alternatively, the UV lamp may be a UV light emitting diode (LED), which may be based on AlGaAs or GaN.

Still referring to FIG. 4, in some embodiments processor 70 may be in communication with valve controller 86; alternatively, valve controller 86 may be part of the functionality of processor 70. Valve controller 86 controls the actuation of any valves that may be used to control the flow of DSR solution between the reservoir, the peritoneal cavity, and the bladder. For example, as described above with reference to FIG. 2B, implantable device 20 may be configured to pump the DSR solution from an external or internal reservoir to the peritoneal cavity, while actuating valves 49 and 49' so as to close fluidic access to the bladder and thus avoid inadvertently pumping fluid from the bladder into the peritoneal cavity; and may be configured to pump fluid from the peritoneal cavity to the bladder, while actuating valves 49 and 49' so as to close fluidic access to the reservoir and thus avoid inadvertently pumping fluid from the peritoneal cavity into the reservoir. Valve controller 86 may coordinate the actuation of valves 49 and 49' in such a manner, or in any other appropriate manner based on the particular valve configuration.

Referring now to FIGS. 4A and 4B, further details of an exemplary embodiment of implantable device 20 are provided. In FIG. 4A, housing 91 appears transparent, although it should of course be understood that housing 91 comprises an opaque biocompatible plastic, glass and/or metal alloy materials. In FIG. 4B, the implantable device is shown with lower portion 92 of housing 91 removed from upper housing 93 and without a glass bead/epoxy filler material that is used to prevent moisture from accumulating in the device. In FIGS. 4A and 4B, motor 94 is coupled to gear pump housing 95, which is described in greater detail with respect to FIG. 5A. The electronic components discussed above with respect to FIG. 3 are disposed on circuit board substrate 96, which extends around and is fastened to support member 97. Coil 98 (corresponding to coil 84 of FIG. 3) is disposed on flap 99 of the substrate and is coupled to the electronic components on flap 100 by flexible cable portion 101. Support member 97 is fastened to upper housing 93 and provides a cavity that holds battery 102 (corresponding to battery 74 of FIG. 3). Lower portion 92 of housing 91 includes port 103 for injecting the glass bead/epoxy mixture after upper portion 93 and lower portion 92 of housing 91 are fastened together, to reduce space in the housing in which moisture can accumulate.

Housing 91 also may include features designed to reduce movement of the implantable pump once implanted within a patient, such as a suture hole to securely anchor the implantable device to the surrounding tissue. Housing 91 may in addition include a polyester ingrowth patch that facilitates attachment of the implantable device to the surrounding tissue following subcutaneous implantation.

Additionally, the implantable device optionally may incorporate anti-clogging agents, such enzyme eluting materials that specifically target the proteinaceous components of fluid from the peritoneal cavity, enzyme eluting materials that specifically target the proteinaceous and encrustation promoting components of urine, chemical eluting surfaces, coatings that prevent adhesion of proteinaceous compounds, and combinations thereof. Such agents, if provided, may be integrated within or coated upon the surfaces of the various components of the system.

Figures 5A, 5B, 5C, 5D:
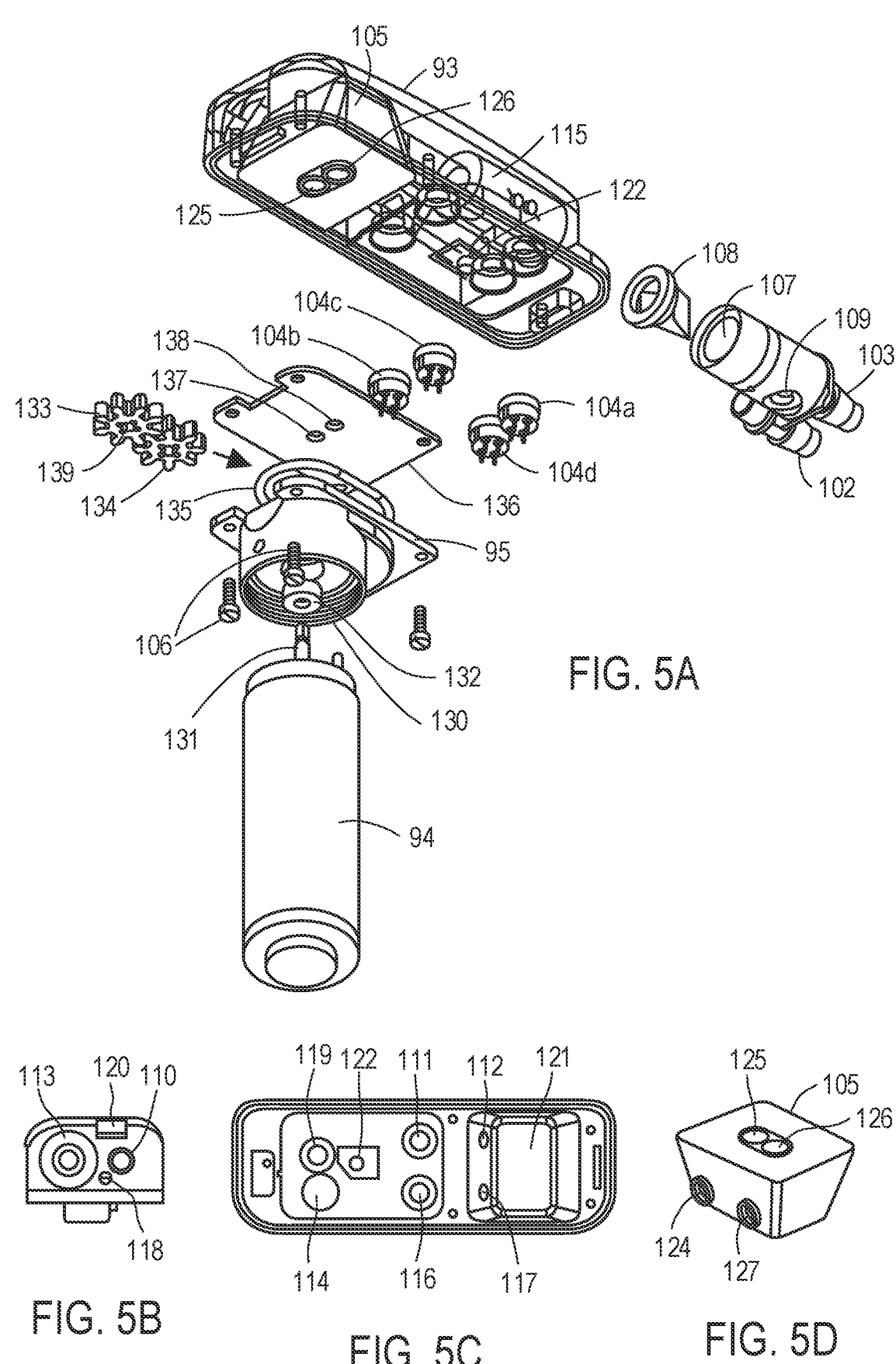
FIGS. 5A, 5B, 5C and 5D are, respectively, an exploded perspective view of the drive assembly of the implantable device; front and plan views of the upper housing; and a perspective view of the manifold of an exemplary embodiment of the implantable device.

Referring now to FIGS. 5A to 5D, further details of the gear pump and fluid path are described. In FIGS. 5A-5D, like components are identified using the same reference numbers from FIGS. 4A and 4B. FIG. 5A is an exploded view showing assembly of motor 94 with gear pump housing 95 and upper housing 93, as well as the components of the fluid path within the implantable device. Upper housing 93 preferably comprises a high strength plastic or metal alloy material that can be molded or machined to include openings and channels to accommodate inlet nipple 102, outlet nipple 103, pressure sensors 104a-104d, manifold 105 and screws 106. Nipples 102 and 103 preferably are machined from a high strength biocompatible metal alloy, and outlet nipple 103 further includes channel 107 that accepts elastomeric duckbill valve 108. Outlet nipple 103 further includes lateral recess 109 that accepts pressure sensor 104a, which is arranged to measure pressure at the inlet end of the bladder catheter, corresponding to pressure in the patient's bladder (or peritoneal cavity).

Referring now also to FIGS. 5B and 5C, inlet nipple 102 is disposed within opening 110, which forms a channel in upper housing 93 that includes opening 111 for pressure sensor 104b and opening 112 that couples to manifold 105. Pressure sensor 104b is arranged to measure the pressure at the outlet end of the peritoneal catheter, corresponding to pressure in the peritoneal cavity. Outlet nipple 103, including duckbill valve 107, is disposed within opening 113 of upper housing 93 so that lateral recess 108 is aligned with opening 114 to permit access to the electrical contacts of pressure sensor 104a. Opening 113 forms channel 115 that includes opening 116 for pressure sensor 104c, and opening 117 that couples to manifold 105. Upper housing 93 preferably further includes opening 118 that forms a channel including opening 119 for accepting pressure sensor 104d. Pressure sensor 104d measures ambient pressure, and the output of this sensor is used to calculate differential pressures as described above. Upper housing further includes notch 120 for accepting connector 26 (see FIG. 5B) for retaining the peritoneal and bladder catheters coupled to inlet and outlet nipples 102 and 103. Upper housing 93 further includes recess 121 to accept manifold 105, and peg 122, to which support member 97 (see FIG. 4B) is connected.

Manifold 105 preferably comprises a molded elastomeric component having two separate fluid channels (such channels designated 88 in FIG. 4B) that couple inlet and outlet flow paths through upper housing 93 to the gear pump. The first channel includes inlet 124 and outlet 125, while the second channel includes inlet 126 and outlet 127. Inlet 124 couples to opening 112 (see FIG. 5C) of the peritoneal path and outlet 127 couples to opening 117 of the bladder path. Analyte sensor 85 (see FIG. 4B) may be located in communication with the peritoneal fluid path, or optionally located on catheter 23. Manifold 105 is configured to improve manufacturability of the implantable device, by simplifying construction of upper housing 93 and obviating the need to either cast or machine components with complicated non-linear flow paths.

Motor 94 is coupled to gear pump housing 95 using mating threads 130, such that splined shaft 131 of motor 94 passes through bearing 132. The gear pump of the present invention comprises intermeshing gears 133 and 134 enclosed in gear pump housing 95 by O-ring seal 135 and plate 136. The gear pump is self-priming. Plate 136 includes openings 137 and 138 that mate with outlet 125 and inlet 126 of manifold 105, respectively. Splined shaft 131 of motor 94 extends into opening 139 of gear 133 to provide floating engagement with that gear.

Peritoneal and Bladder Catheters

Figures 6A, 6B, 7A, 7B:
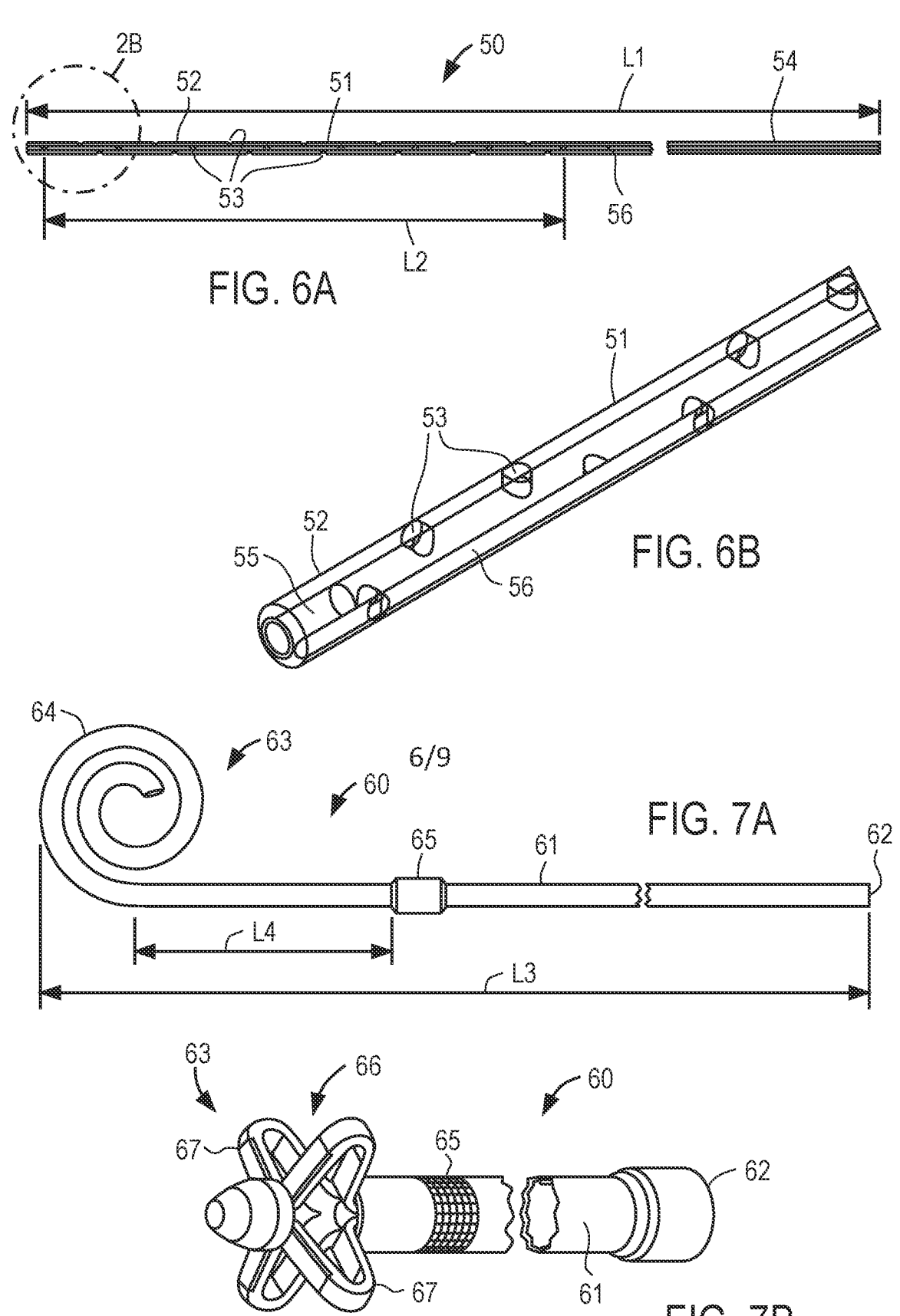
FIGS. 6A and 6B are, respectively, side view and perspective detailed views of an exemplary embodiment of a peritoneal catheter suitable for use with system of FIG. 1, in which FIG. 6B corresponds to distal region of FIG. 6A.
FIGS. 7A and 7B are, respectively, side and perspective views, respectively, of first and second embodiments of bladder catheters suitable for use with the system of FIG. 1.

Referring to FIGS. 6A and 6B, peritoneal catheter 50 may be Medionics International Inc.'s peritoneal dialysis Catheter, Model No. PSNA-100 or a catheter having similar structure and functionality. Peritoneal catheter 50 corresponds to peritoneal catheter 23 of FIGS. 2A-2B, and may comprise tube 51 of medical-grade silicone including inlet (distal) end 52 having a plurality of through-wall holes 53 and outlet (proximal) end 54. Holes 53 may be arranged circumferentially offset by about 90 degrees, as shown in FIG. 6B. Peritoneal catheter 50 may also include a polyester cuff (not shown) in the region away from holes 53, to promote adhesion of the catheter to the surrounding tissue, thereby anchoring it in place. Alternatively, inlet end 52 of peritoneal catheter 50 may have a spiral configuration, and an atraumatic tip, with holes 53 distributed over a length of the tubing to reduce the risk of clogging.

Inlet end 52 also may include a polyester cuff to promote adhesion of the catheter to an adjacent tissue wall, thereby ensuring that the inlet end of the catheter remains in position. Outlet end 54 also may include a connector for securing the outlet end of the peritoneal catheter to implantable device 20. In one preferred embodiment, the distal end of the peritoneal catheter, up to the ingrowth cuff, may be configured to pass through a conventional 16F peel-away sheath. In addition, the length of the peritoneal catheter may be selected to ensure that it lies along the bottom of the body cavity, and is sufficiently resistant to torsional motion so as not to become twisted or kinked during or after implantation.

With respect to FIG. 7A, a first embodiment of bladder catheter 60 is described, corresponding to bladder catheter 25 of FIGS. 2A-2B. Bladder catheter 60 preferably comprises tube 61 of medical-grade silicone having inlet (proximal) end 62 and outlet (distal) end 63 including spiral structure 64, and polyester ingrowth cuff 65. Bladder catheter 60 includes a single internal lumen that extends from inlet end 62 to a single outlet at the tip of spiral structure 64, commonly referred to as a "pigtail" design. Inlet end 62 may include a connector for securing the inlet end of the bladder catheter to implantable device 20, or may have a length that can be trimmed to fit a particular patient. In one embodiment, bladder catheter 60 may have length L3 of about 45 cm, with cuff 65 placed length L4 of about 5 to 6 cm from spiral structure 64. Bladder catheter 60 may be loaded onto a stylet with spiral structure 64 straightened, and implanted using a minimally invasive technique in which outlet end 63 and spiral structure 64 are passed through the wall of a patient's bladder using the stylet. When the stylet is removed, spiral structure 64 returns to the coiled shape shown in FIG. 7A. Once outlet end 63 of bladder catheter 60 is disposed within the patient's bladder, the remainder of the catheter is implanted using a tunneling technique, such that inlet end 62 of the catheter may be coupled to implantable device 20. Spiral structure 64 may reduce the risk that outlet end 63 accidentally will be pulled out of the bladder before the tissue surrounding the bladder heals sufficiently to incorporate ingrowth cuff 65, thereby anchoring the bladder catheter in place.

In a preferred embodiment, bladder catheter 60 is configured to pass through a conventional peel-away sheath. Bladder catheter 60 preferably is sufficiently resistant to torsional motion so as not to become twisted or kinked during or after implantation. In a preferred embodiment, peritoneal catheter 50 and bladder catheter 60 preferably are different colors, have different exterior shapes (e.g., square and round) or have different connection characteristics so that they cannot be inadvertently interchanged during connection to implantable device 20. Optionally, bladder catheter 60 may include an internal duckbill valve positioned midway between inlet 62 and outlet end 63 of the catheter to ensure that urine does not flow from the bladder into the peritoneal cavity if the bladder catheter is accidentally pulled free from the pump connector of implantable device 20.

In an alternative embodiment, the peritoneal and bladder catheters devices may incorporate one or several anti-infective agents to inhibit the spread of infection between body cavities. Examples of anti-infective agents which may be utilized may include, e.g., bacteriostatic materials, bactericidal materials, one or more antibiotic dispensers, antibiotic eluting materials, and coatings that prevent bacterial adhesion, and combinations thereof. Additionally, implantable device 20 may include a UV lamp configured to irradiate fluid in the peritoneal and/or bladder catheters so as to kill any pathogens that may be present and thus inhibit the development of infection.

Alternatively, rather than comprising separate catheters, peritoneal and bladder catheters 50, 60 may share a common wall, which may be convenient because the bladder and peritoneal cavity share a common wall, thereby facilitating insertion of a single dual-lumen tube. In addition, either or both of the peritoneal or bladder catheters may be reinforced along a portion of its length or along its entire length using ribbon or wire braiding or lengths of wire or ribbon embedded or integrated within or along the catheters. The braiding or wire may be fabricated from metals such as stainless steels, superelastic metals such as nitinol, or from a variety of suitable polymers. Such reinforcement may also be used for catheter 46 connected to optional reservoir 45.

With respect to FIG. 7B, a second embodiment of a bladder catheter is described, in which similar components are identified with like-primed numbers. Bladder catheter 60' preferably comprises tube 61' of medical-grade silicone having inlet end 62', outlet end 63' and polyester ingrowth cuff 65'. In accordance with this embodiment, outlet end 63' includes malecot structure 66, illustratively comprising four resilient wings 67 that expand laterally away from the axis of the catheter to reduce the risk that outlet end 63' of the catheter will be inadvertently pulled loose after placement. Inlet end 62' may include a connector for securing the inlet end of the bladder catheter to implantable device 20, or may have a length that can be trimmed to fit a particular patient.

Malecot structure 66 preferably is constructed so that wings 67 deform to a substantially flattened configuration when a stylet is inserted through the lumen of the catheter. In this manner, bladder catheter 60' may be loaded onto a stylet, and using a minimally invasive technique, outlet end 63' and malecot structure 66 may be passed through the wall of a patient's bladder using the stylet. When the stylet is removed, wings 67 of the malecot structure return to the expanded shape shown in FIG. 7B. Once outlet end 63' of bladder catheter 60' is coupled to the patient's bladder, the remainder of the catheter is implanted using a tunneling technique, such that inlet end 62' of the catheter may be coupled to implantable device 20. Malecot structure 66 may reduce the risk that outlet end 63' accidentally will be pulled out of the bladder before the tissue surrounding the bladder heals sufficiently to incorporate ingrowth cuff 65'. As for the embodiment of FIG. 7A, the bladder catheter of FIG. 7B may be configured to pass through a conventional peel-away sheath, and preferably is sufficiently resistant to torsional motion so as not to become twisted or kinked during or after implantation.

The Charging and Communication System

Figures 8A, 8B, 9:
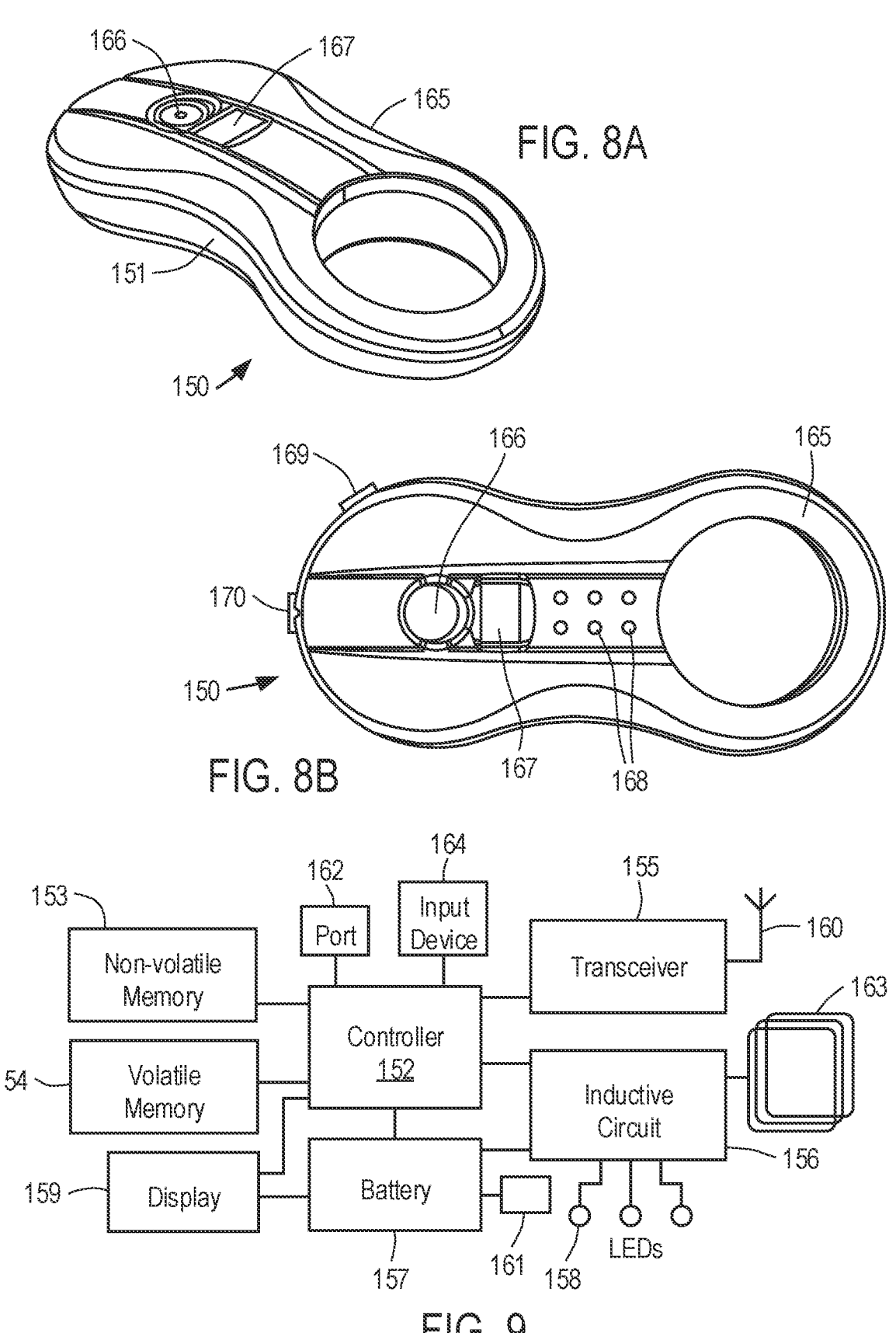
FIGS. 8A and 8B are, respectively, perspective and top views of the handpiece portion of an exemplary charging and communication system for use in practicing the methods of the present invention.
FIG. 9 is a schematic diagram of the electronic components of an exemplary embodiment of the charging and communication system for use in practicing the methods of the present invention.

Referring to FIGS. 8A, 8B and 9, charging and communication system 150 (corresponding to system 30 of FIG. 1) is described in greater detail. In one preferred embodiment, charging and communication system 150 comprises handpiece 151 and base 31 (see FIG. 1). Base 31 provides comprises a cradle for recharging handpiece 151, and preferably contains a transformer and circuitry for converting conventional 120/220/240V power service to a suitable DC current to charge handpiece 151 when it is coupled to the base. Alternatively, handpiece 151 may include circuitry for charging the handpiece battery, and a detachable power cord. In this embodiment, handpiece 151 may be directly plugged into a wall socket for charging, and the power cord removed when the handpiece is used to recharge the implantable device.

As shown in FIG. 9, handpiece 151 contains controller 152, illustratively the processor of a micro-controller unit coupled to nonvolatile memory 153 (e.g., either EEPROM or flash memory), volatile memory 154, radio transceiver 155, inductive circuit 156, battery 157, indicator 158 and display 159. Controller 152, memories 153 and 154, and radio transceiver 155 may be incorporated into a single microcontroller unit, such as the MPS430 family of microprocessors, available from Texas Instruments Incorporated, Dallas, Tex. Transceiver 155 is coupled to antenna 160 for sending and receiving information to implantable device 20. Battery 157 is coupled to connector 161 that removably couples with a connector in base 31 to recharge the battery. Port 162, such as a USB port or comparable wireless circuit, is coupled to controller 152 to permit information to be exchanged between handpiece 151 and the monitoring and control system. Inductive circuit 156 is coupled to coil 163. Input device 164, preferably a multi-function button, also is coupled to controller 152 to enable a patient to input a limited number of commands. Indicator 158 illustratively comprises a plurality of LEDs that illuminate to indicate the quality of charge coupling achieved between the handpiece and implantable device, and therefore assist in optimizing the positioning of handpiece 151 relative to the implantable device during recharging. In one preferred embodiment, indicator 158 is omitted, and instead a bar indicator provided on display 159 that indicates the quality-of-charging resulting from the coupling of coils 163 and 84.

In a preferred embodiment, handpiece 151 includes a device identifier stored in nonvolatile memory 153 that corresponds to the device identifier stored in nonvolatile memory 71 of the implantable device, such that handpiece 151 will communicate only with its corresponding implantable device 20. Optionally, a configurable handpiece for use in a physician's office may include the ability to interrogate an implantable device to request that device's unique device identifier, and then change the device identifier of the monitoring and control system 40 to that of the patient's implantable device, so as to mimic the patient's handpiece.

In this way, a physician may adjust the configuration of the implantable device if the patient forgets to bring his handpiece 151 with him during a visit to the physician's office.

Controller 152 executes firmware stored in nonvolatile memory 153 that controls communications and charging of the implantable device. Controller 152 also is configured to transfer and store data, such as event logs, uploaded to handpiece 151 from the implantable device, for later retransmission to monitoring and control system 40 via port 162, during physician office visits. Alternatively, handpiece 151 may be configured to recognize a designated wireless access point within the physician's office, and to wirelessly communicate with monitoring and control system 40 during office visits. As a further alternative, base 31 may include telephone circuitry for automatically dialing and uploading information stored on handpiece 151 to a physician's website via a secure connection, such as alarm information.

Controller 152 preferably includes a low-power mode of operation and includes an internal clock, such that the controller periodically awakens to communicate with the implantable device to log data or to perform charging functions. Controller 152 preferably is configured to awaken when placed in proximity to the implantable device to perform communications and charging functions, and to transmit commands input using input device 164. Controller 152 further may include programming for evaluating information received from the implantable device, and generating an alarm message on display 159. Controller 152 also may include firmware for transmitting commands input using input device 164 to the implantable device, and monitoring operation of the implantable device during execution of such commands, for example, during boost or jogging/shaking operation of the gear pump to clear a blockage. In addition, controller 152 controls and monitors various power operations of handpiece 151, including operation of inductive circuit 156 during recharging of the implantable device, displaying the state of charge of battery 74, and controlling charging and display of state of charge information for battery 157.

Nonvolatile memory 153 preferably comprises flash memory or EEPROM, and stores the unique device identifier for its associated implantable device, firmware to be executed by controller 152, configuration set point, and optionally, coding to be executed on transceiver 155 and/or inductive circuit 156. Firmware and set point data stored on nonvolatile memory 153 may be updated using information supplied by control and monitoring system 40 via port 162. Volatile memory 154 is coupled to and supports operation of controller 152, and stores data and event log information uploaded from implantable device 20.

In addition, in a preferred embodiment, nonvolatile memory 153 stores programming that enables the charging and communication system to perform some initial start-up functions without communicating with the monitor and control system. In particular, memory 153 may include routines that make it possible to test the implantable device during implantation using the charging and communication system alone in a "self-prime mode" of operation. In this case, a button may be provided that allows the physician to manually start the pump, and display 159 is used to provide feedback whether the pumping session was successful or not. Display 159 of the charging and communication system also may be used to display error messages designed to assist the physician in adjusting the position of the implantable device or peritoneal or bladder catheters. These functions preferably are disabled after the initial implantation of the implantable device.

Transceiver 155 preferably comprises a radio frequency transceiver, e.g., conforming to the Bluetooth or IEEE 802.11 wireless standards, and is configured for bi-directional communications via antenna 160 with transceiver circuit 76 disposed in the implantable device. Transceiver 155 also may include a low power mode of operation, such that it periodically awakens to listen for incoming messages and responds only to those messages including the unique device identifier assigned to its associated implantable device. Transceiver 155 preferably employs an encryption routine to ensure that messages sent to, or received from, the implantable device cannot be intercepted or forged.

Inductive circuit 156 is coupled to coil 163, and is configured to inductively couple with coil 84 of the implantable device to recharge battery 74 of the implantable device. In one embodiment, inductive circuit 156 is coupled to indicator 158, preferably a plurality of LEDs that light to indicate the extent of magnetic coupling between coils 163 and 84 (and thus quality of charging), thereby assisting in positioning handpiece 151 relative to the implantable device. In one preferred embodiment, inductive coils 84 and 163 are capable of establishing good coupling through a gap of 35 mm, when operating at a frequency of 315 kHz or less. In an embodiment in which implantable device includes optional infrared LED 83, charging and communication system 30 may include an optional infrared sensor (not shown) which detects that infrared light emitted by LED 83 and further assists in positioning handpiece 151 to optimize magnetic coupling between coils 163 and 84, thereby improving the energy transmission to the implantable device.

Controller 152 also may be configured to periodically communicate with the implantable device to retrieve temperature data generated by temperature sensor 78 and stored in memory 72 during inductive charging of battery 74. Controller 152 may include firmware to analyze the battery temperature, and to adjust the charging power supplied to inductive circuit 163 to maintain the temperature of the implantable device below a predetermined threshold, e.g., less than 2 degrees C. above body temperature. That threshold may be set to reduce thermal expansion of the battery and surrounding electronic and mechanical components, for example, to reduce thermal expansion of motor and gear pump components and to reduce the thermal strain applied to the seal between lower portion 92 of housing and upper housing 93. In a preferred embodiment, power supplied to inductive coil 163 is cycled between high power (e.g., 120 mA) and low power (e.g., 40 mA) charging intervals responsive to the measured temperature within the implantable device.

As discussed above with respect to inductive circuit 75 of the implantable device, inductive circuit 156 optionally may be configured to transfer additional power to motor 73 of the implantable device, via inductive circuit 75 and battery 74, in a "boost" mode or jogging mode to unblock the gear pump. In particular, if an alarm is transmitted to controller 152 that motor 73 is stalled, e.g., due to a block created by viscous fluid, the patient may be given the option of using input device 164 to apply an overvoltage to motor 73 from inductive circuit 75 for a predetermined time period to free the blockage. Alternatively, activating input device 164 may cause controller 152 to command processor 70 to execute a routine to jog or shake the gear pump by rapidly operating motor 74 in reverse and forward directions to disrupt the blockage. Because such modes of operation may employ higher energy consumption than expected during normal operation, inductive circuits 156 and 75 may be configured to supply the additional energy for such motor operation directly from the energy stored in battery 157, instead of depleting battery 74 of the implantable device.

Battery 157 preferably comprises a lithium ion or lithium polymer battery capable of long lasting operation, e.g., up to three years. Battery 157 has sufficient capacity to supply power to handpiece 151 to operate controller 152, transceiver 155, inductive circuit 156 and the associated electronics while disconnected from base 31 and during charging of the implantable device. In a preferred embodiment, battery 157 has sufficient capacity to fully recharge battery 74 of the implantable device from a depleted state in a period of about 2-4 hours. Battery 157 also should be capable of recharging within about 2-4 hours. It is expected that for daily operation moving 700 ml of fluid, battery 157 and inductive circuit 156 should be able to transfer sufficient charge to battery 74 via inductive circuit 75 to recharge the battery within about 30 minutes. Battery capacity preferably is supervised by controller 152 using a charge accumulator algorithm.

Referring again to FIGS. 8A and 8B, handpiece 151 preferably includes housing 165 having multi-function button 166 (corresponding to input device 164 of FIG. 9) and display 167 (corresponding to display 159 of FIG. 9). A plurality of LEDs 168 is disposed beneath a translucent portion of handpiece 151, and corresponds to indicator 158 of FIG. 9. Port 169 enables the handpiece to be coupled to monitoring and control system 40 (and corresponds to port 162 of FIG. 9), while connector 170 (corresponding to connector 161 in FIG. 9) permits the handpiece to be coupled to base 31 to recharge battery 157. Multi-function button 166 provides the patient the ability to input a limited number of commands to the implantable device. Display 167, preferably an OLED or LCD display, provides visible confirmation that a desired command input using multifunction button 166 has been received. Display 167 also may display the status and state of charge of battery 74 of the implantable device, the status and state of charge of battery 157 of handpiece 151, signal strength of wireless communications, quality-of-charging, error and maintenance messages. Inductive coil portion 171 of housing 165 houses inductive coil 163.

LEDs 168 are visible through the material of housing 165 when lit, and preferably are arranged in three rows of two LEDs each. During charging, the LEDs light up to display the degree of magnetic coupling between inductive coils 163 and 84, e.g., as determined by energy loss from inductive circuit 156, and may be used by the patient to accurately position handpiece 151 relative to the implantable device. Thus, for example, a low degree of coupling may correspond to lighting of only two LEDs, an intermediate degree of coupling with lighting of four LEDs, and a preferred degree of coupling being reflected by lighting of all six LEDs. Using this information, the patient may adjust the position of handpiece 151 over the area where implantable device is located to obtain a preferred position for the handpiece, resulting in the shortest recharging time. In one preferred embodiment, LEDs 168 are replaced with an analog bar display on display 167, which indicates the quality of charge coupling.

Monitoring and Control System

Figure 10:
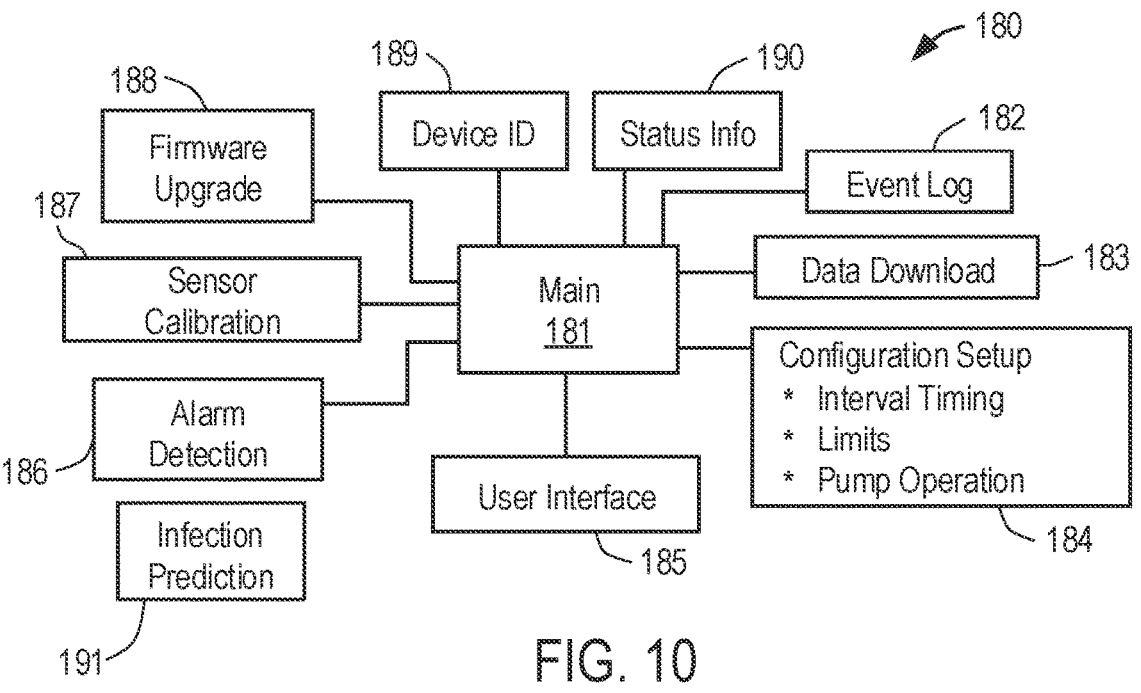
FIG. 10 is a schematic diagram of the software implementing the monitoring and control system for use in practicing the methods of the present invention.
Figure 11:
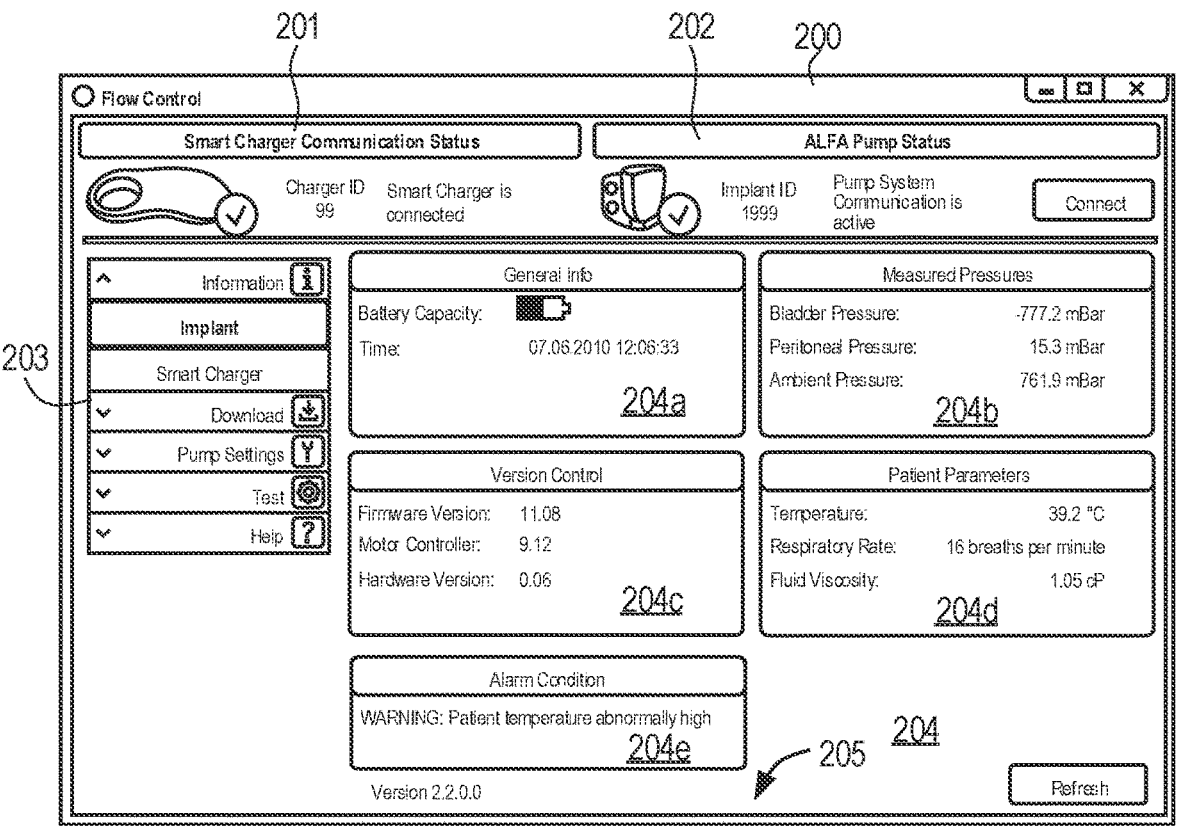
FIG. 11 is a screen display of the main screen that is displayed to a physician running monitoring and control software.

Turning to FIG. 10, the software implementing monitoring and control system of FIG. 1 will now be described. Software 180 comprises a number of functional blocks, schematically depicted in FIG. 10, including main block 184, event logging block 182, data download block 183, configuration setup block 184, user interface block 185, alarm detection block 186 including health monitor block 191 and analyte monitoring block 192, sensor calibration block 187, firmware upgrade block 188, device identifier block 189 and status information block 190. In one embodiment, the software is coded in C++ and employs an object oriented format, although other software languages and environments could be used. In one embodiment, the software is configured to run on top of a Microsoft Windows® (a registered trademark of Microsoft Corporation, Redmond, Wash.) or Unix-based operating system, such as are conventionally employed on desktop and laptop computers, although other operating systems could be employed.

The computer running monitoring and control system software 180 preferably includes a data port, e.g., USB port or comparable wireless connection that permits handpiece 151 of the charging and communication system to be coupled via port 169. Alternatively, as discussed above, the computer may include a wireless card, e.g., conforming to the IEEE 802.11 standard, thereby enabling handpiece 151 to communicate wirelessly with the computer running software 180. As a further alternative, the charging and communication system may include telephony circuitry that automatically dials and uploads data, such as alarm data, from handpiece 151 to a secure website accessible by the patient's physician.

Main block 184 preferably consists of a main software routine that executes on the physician's computer, tablet or smartphone, and controls overall operation of the other functional blocks. Main block 184 enables the physician to download event data and alarm information stored on handpiece 151 to their computer, tablet or smartphone, and also permits control and monitoring software 180 to directly control operation of the implantable device when coupled to handpiece 151. Main block also enables the physician to upload firmware updates and configuration data to the implantable device.

Event Log block 182 is a record of operational data downloaded from the implantable device via the charging and communication system, and may include, for example, pump start and stop times, motor position, sensor data for the peritoneal cavity and bladder pressures, patient temperature, respiratory rate or fluid temperature, pump outlet pressure, humidity, pump temperature, battery current, battery voltage, battery status, and the like. The event log also may include the occurrence of events, such as pump blockage, operation in boost or jog modes, alarms or other abnormal conditions.

Data Download block 183 is a routine that handles communication with handpiece 151 to download data from volatile memory 154 after the handpiece is coupled to the computer running monitoring and control software 180. Data Download block 183 may initiates, either automatically or at the instigation of the physician via user interface block 185, downloading of data stored in the event log.

Configuration Setup block 184 is a routine that configures the parameters stored within nonvolatile memory 71 that control operation of the implantable device. The interval timing parameters may determine, e.g., how long the processor remains in sleep mode prior to being awakened to listen for radio communications or to control pump operation. The interval timing parameters may control, for example, the duration of pump operation to move fluid from the peritoneal cavity to the bladder and the interval between periodic tick movements that inhibit blockage of the implantable device and peritoneal and bladder catheters. Interval timing settings transmitted to the implantable device from monitoring and control software 180 also may determine when and how often event data is written to nonvolatile memory 71, and to configure timing parameters used by the firmware executed by processor 152 of handpiece 151 of the charging and communication system. Block 184 also may be used by the physician to configure parameters stored within nonvolatile memory 71 relating to limit values on operation of processor 70 and motor 73, and to set target and threshold values. These values may include the sodium concentration detected in the peritoneal catheter at which fluid transfer to the bladder should be initiated, maximum DSR solution dwell time, minimum and maximum pressures at the peritoneal and bladder catheters, the maximum temperature differential during charging, times when the pump may and may not operate, etc. The limit values set by block 184 also configure parameters that control operation of processor 152 of handpiece 151.

Block 184 also may configure parameters store within nonvolatile memory 71 of the implantable device relating to control of operation of processor 70 and motor 73. These values may include target volumes of fluid to transport, volume of fluid to be transported per pumping session, motor speed and duration per pumping session. Block 184 also may specify the parameters of operation of motor 73 during boost mode of operation, when coupled to handpiece 151, and shake/jog modes of operation when the implantable device is run using battery 74 alone. Such parameters may include motor speed and voltage, duration/number of revolutions of the motor shaft when alternating between forward and reverse directions, etc.

User interface block 185 handles display of information retrieved from the monitoring and control system and implantable device via data download block 183, and presents that information in an intuitive, easily understood format for physician review. As described below with respect to FIG. 11, such information may include status of the implantable device, status of the charging and control system, measured pressures, volume of fluid transported per pumping session or per day, etc. User interface block 185 also generates user interface screens that permit the physician to input information to configure the interval timing, limit and pump operation parameters discussed above with respect to block 184.

Alarm detection block 186 may include a routine for evaluating the data retrieved from the implantable device or charging and communication system, and flagging abnormal conditions for the physician's attention. For example, alarm detection block 186 may include health monitor block 191, which is configured to alert the physician to any changes in the patient's health that may warrant changing the volume, time, and/or frequency with which the DSR therapy is conducted.

Sensor calibration block 187 may include a routines for testing or measuring drift, of sensors 70, 78-81 and 85 employed in the implantable device, e.g., due to aging or change in humidity. Block 187 may then compute offset values for correcting measured data from the sensors, and transmit that information to the implantable device for storage in nonvolatile memory 71. For example, pressure sensors 104a-104d may experience drift due to aging or temperature changes. Block 187 accordingly may compute offset values that are then transmitted and stored in the implantable device to account for such drift.

Firmware upgrade block 188 may comprise a routine for checking the version numbers of the processor or motor controller firmware installed on the implantable device and/or processor firmware on charging and communication system, and identify whether upgraded firmware exists. If so, the routine may notify the physician and permit the physician to download revised firmware to the implantable device for storage in nonvolatile memory 71 or to download revised firmware to the charging and communication system for storage in nonvolatile memory 153.

Device identifier block 189 consists of a unique identifier for the implantable device that is stored in nonvolatile memory 71 and a routine for reading that data when the monitoring and control system is coupled to the implantable device via the charging and communication system. As described above, the device identifier is used by the implantable device to confirm that wireless communications received from a charging and communication system are intended for that specific implantable device. Likewise, this information is employed by handpiece 151 of the charging and communication system in determining whether a received message was generated by the implantable device associated with that handpiece. Finally, the device identifier information is employed by monitoring and control software 180 to confirm that the handpiece and implantable device constitute a matched set.

Status information block 190 comprises a routine for interrogating implantable device, when connected via handpiece 151, to retrieve current status date from the implantable device, and/or handpiece 151. Such information may include, for example, battery status, the date and time on the internal clocks of the implantable device and handpiece, version control information for the firmware and hardware currently in use, and sensor data.

Referring now to FIG. 10, an exemplary screen shot generated by user interface block 187 of software 180 is described for an implantable system used in accordance with the methods of the present invention. FIG. 10 shows main screen 200 that is displayed to a physician running monitoring and control software 180. Main screen 200 includes a status area that displays status information retrieved from the implantable device and the charging and communication system by the routine corresponding to block 190 of FIG. 10. More particularly, the status area includes status area 201 for the charging and communication system (referred to as the "Smart Charger) and status area 202 for the implantable device (referred to as the "ALFA Pump"). Each status area includes an icon showing whether the respective system is operating properly, indicated by a checkmark, the device identifier for that system, and whether the system is connected or active. If a parameter is evaluated by the alarm detection block 186 to be out of specification, the icon may instead include a warning symbol. Menu bar 203 identifies the various screens that the physician can move between by highlighting the respective menu item. Workspace area 204 is provided below the status area, and includes a display that changes depending upon the menu item selected. Below workspace area 204, navigation panel 205 is displayed, which includes the version number of software 180 and a radio button that enables the displays in workspace area 204 to be refreshed.

In FIG. 10, the menu item "Information" with submenu item "Implant" is highlighted in menu bar 203. For this menu item selection, workspace area 204 illustratively shows, for the implantable device, battery status window 204a, measured pressures window 204b and firmware version control window 204c. Battery status window 204a includes an icon representing the charge remaining in battery 74, and may be depicted as full, three-quarters, one-half, one-quarter full or show an alarm that the battery is nearly depleted. The time component of window 204a indicates the current time as received from the implantable device, where the date is expressed in DD/MM/YYYY format and time is expressed in HR/MIN/SEC format based on a 24 hour clock. Measured pressures window 204b displays the bladder pressure, peritoneal pressure and ambient pressures in mBar measured by sensors 104a, 104b and 104d respectively (see FIG. 5A). Version control window 204c indicates the firmware version for processor 70, for the motor controller, and the hardware version of the implantable device. Patient parameters window 204d displays the patient's temperature, respiratory rate, and intra-abdominal pressure. Note that if implantable device included other types of sensors, e.g., sensors that measure the levels of fluid in the body, then the parameters measured by such sensors could also be displayed in window 204d.

Alarm condition window 204e displays any changes in parameters that may indicate a change in the patient's health, such as the possible development of heart failure decompensation or an improvement or worsening of the patient's health (Blocks 191 and 192 in FIG. 10). For example, as illustrated, alarm condition window 204e may alert the physician that the patient's intra-abdominal pressure is abnormally high, so that the physician then may follow up with the patient. In some embodiments, based on information displayed in windows 204b, 204d, and/or 204e, the physician may adjust the operating parameters of the pump.

Methods of using the inventive implantable systems, such as illustrated in FIGS. 2A and 2B, are now described with reference to FIG. 12. Method 250 includes introducing no or low sodium DSR solution into the peritoneal cavity from a reservoir that is internal or external to the patient's body (step 252). For example, as described above with reference to FIG. 2A, the DSR solution may be introduced using an external pump or gravity. Or, as described above with reference to FIG. 2B, the DSR solution may be introduced using implantable device 20 and one or more valves in communication therewith. A sufficient amount of DSR solution is introduced into the peritoneal cavity of the patient and allowed to dwell therein until a target analyte concentration, such as sodium, is detected using analyte sensor 85 or until a maximum dwell time is attained. As described hereinabove, the goal of the DSR solution is to draw sodium from the patient's body tissues into the peritoneal cavity and cause osmotic ultrafiltrate to accumulate in the peritoneal cavity, from which it then is moved to the bladder via implantable device 20.

In step 254, the analyte concentration in the patient's peritoneal cavity is monitored using the analyte sensor. The pressure in the patient's peritoneal cavity and bladder also are monitored. At step 256, the measured sodium concentration in the DSR solution and fluid accumulated in the peritoneal cavity is compared to a target value, e.g., a percentage of the patient's blood serum sodium level based on a blood sample taken before the DSR therapy session. Such a predetermined measured sodium level may be used to select a target value at which to initiate pumping because the sodium concentration in the peritoneal cavity will not exceed that value during the DSR therapy session. The target value may be downloaded to implantable device by the physician using software monitoring and control system 40 via external charging and communication system 30 prior to initiating the DSR therapy session (see FIG. 1). The target value may be static, i.e., programmed one time, or may be revised prior to each DSR therapy session based on prior results for that patient and titrated to provide a targeted blood sodium serum level by completion of the DSR therapy session. Alternatively, the target value may consist of a target quantity of sodium to be removed during the DSR therapy session, or a target value of an infusate concentration at which pumping is to begin and/or cease.

If at step 256 the detected analyte concentration is less than the target value ("No branch at step 256), the processor of implantable device 20 then will evaluate at step 258 whether the current dwell time for the DSR solution exceeds the maximum dwell time for that DSR therapy session. The maximum dwell time may be a static value that is programmed once, or a value that is set prior to each DSR therapy session as may be determined by the physician. If the current dwell time is less than the maximum value ("No" branch at step 258), the processor may internally set another time interval, e.g., 5 or 10 minutes, after which it will continue to monitor the analyte level at step 254 and evaluate whether the target has been attained at step 256. If however, the maximum dwell time has been exceeded at step 258, then the processor will activate the pump of implantable device 20 to begin transferring sodium-rich DSR solution and ultrafiltrate from the peritoneal cavity to the patient's bladder, at step 260 ("Yes" branch at step 258). Referring back to the decision box at step 256, if the analyte concentration detected by analyte sensor 85 equals or exceeds the target value (the Yes branch at step 256), the processor also will activate the pump of implantable device 20 at step 260.

Once the pump of implantable device 20 is activated, it will transfer fluid from the peritoneal cavity to the bladder via catheters 23 and 25. To ensure that the pump motor does not overheat from continuous operation, the pump may run for a predetermined specified interval, e.g., 5 or 10 minutes, then rest for a brief interval, e.g., 2-5 minutes, and then resume operation. If the pump is actuated periodically in this manner to complete removal of the DSR solution and accumulated ultrafiltrate from the peritoneal cavity, for example, as determined by the pressure in the peritoneal cavity falling below a target value, the processor will no longer look for the analyte level to exceed the target level for that particular DSR therapy session. Accordingly, once the target analyte concentration is met or the dwell time exceeded for a particular DSR therapy session, the pump will be actuated intermittently until drainage of the peritoneal cavity is determined to be complete.

Apart from intermittent operation to permit brief periods for the pump to rest, as described above, the processor also monitors the patient's bladder pressure to ensure that transfer of fluid to the bladder is interrupted when the bladder is deemed to be full. Fullness may be determined by the physician receiving oral feedback of discomfort from the patient during initial set-up and programming of implantable device 20. Accordingly, at step 262, bladder pressure is monitored, particularly at times when fluid is being transferred to the bladder. If the bladder pressure is lower than the level associated with bladder fullness, as initially programmed ("No" branch at step 262, the processor next evaluates whether the pressure in the peritoneal cavity is greater than a predetermined target pressure at step 264. The target pressure at step 264 is a pressure determined to correspond to fluid accumulation in the patient's peritoneal cavity, which value may set during initial implantation and then periodically updated by the physician using monitoring and control system 40 during the course of multiple DSR therapy sessions. If at step 264 that peritoneal pressure indicates that peritoneal cavity still contains fluid to be transferred to the bladder, the pump of implantable device 20 will remain active (or if at rest, resume operation) to transfer fluid to the bladder (Yes branch at step 264). If the peritoneal cavity pressure is determined at step 264 to be less than target pressure ("No" branch at step 264), the processor will shut down the pump of the implantable device and store a record reflecting completion of that DSR therapy session in the non-volatile memory for eventual transmission to event log 182 (see FIG. 10).

Referring again to step 262, if the processor of implantable device 20 detects that the pressure of fluid in the patient's bladder exceeds the target value ("Yes branch at step 262), the processor will shut down the pump, ceasing movement of fluid to the patient's bladder. The processor then will set a timer at step 266 during which implantable device 20 waits until the patient voids his bladder. Once the patient voids his bladder and the bladder pressure drops below the target level, the processor again activates the pump to transfer remaining fluid in the peritoneal cavity to the bladder.

As described above, actuation of the pump transfers sodium-laden DSR solution and ultrafiltrate from the peritoneal cavity to the bladder, thereby reducing the level of sodium in the body and causing elimination of excess fluid by i) enhancing normal kidney function through urination and ii) removal to the bladder of osmotic ultrafiltrate that accumulates in the peritoneal cavity. It is expected that by configuring to activate the pump responsive to the analyte level of the fluid in the peritoneal cavity, better control of serum sodium concentration may be maintained than could be achieved by basing the action of the DSR solution on dwell time alone.

Energy may be wirelessly transferred to the implantable device, and data received from the device, using charging and communication system 30 described above with reference to FIG. 1. For example, the implantable device may record parameters reflective of the health of the patient and the operation of the device, which parameters may be communicated to the charging and communication system. The data, e.g., parameters recorded by the implantable device, then is provided to monitoring and control software, which is in communication with the charging and communication system and is under the control of the treating physician. Based on those parameters, the health of the patient may be assessed using the software, and the physician may remotely communicate any modifications to the target analyte concentration, target pressures, flow rates, volume, dwell time, or frequency with which the implantable device is activated to transfer DSR solution and ultrafiltrate containing the extracted sodium to the bladder. Such communication may be performed via the charging and communication system.

While various illustrative embodiments of the invention are described above, it will be apparent to one skilled in the art that various changes and modifications may be made therein without departing from the invention. For example, the implantable device may be ordered differently and may include additional or fewer components of various sizes and composition. The appended claims are intended to cover all such changes and modifications that fall within the true spirit and scope of the invention.

What is claimed is:

1. A system for use with a direct sodium removal (DSR) solution for conducting direct sodium removal therapy in a patient, the system comprising:

an infusate configured to be introduced into a peritoneal cavity, the infusate comprising a solution having a sodium content less than 35 meq/L and (i) from 0.5 to 50 grams dextrose per 100 ml of aqueous solution, (ii) from 0.5 to 50 grams icodextrin/dextrin per 100 ml of aqueous solution, and (iii) purified water;

an analyte sensor configured to output a signal indicative of an analyte concentration associated with the infusate introduced into the peritoneal cavity; and a processor coupled to the analyte sensor and configured to receive the signal indicative of the analyte concentration.

2. The system of claim 1, further comprising an implantable pump, wherein the processor is configured to cause the implantable pump to move fluid from the peritoneal cavity responsive either to the output of the analyte sensor or after expiration of a predetermined dwell time.

3. The system of claim 2, wherein the implantable pump further comprises a transceiver, a battery, an inlet port, and an outlet port.

4. The system of claim 3, further comprising an external charging and communications system for periodically charging the battery and conducting bi-directional data communication via the transceiver.

5. The system of claim 4, wherein the external charging and communications system inductively transfers energy to the implantable pump.

6. The system of claim 2, further comprising:

a peritoneal catheter comprising a first end configured to be disposed in the peritoneal cavity of the patient and a second end configured to be coupled to the implantable pump; and a bladder catheter comprising a first end configured to be coupled to the implantable pump and a second end configured to be disposed in a urinary bladder.

7. The system of claim 6, wherein the analyte sensor measures a concentration of the analyte within at least one of: the implantable pump, the peritoneal catheter, the bladder catheter, or the peritoneal cavity.

8. The system of claim 4, further comprising a monitoring and control system configured to transfer data to the implantable pump via the external charging and communications system.

9. The system of claim 2, wherein the implantable pump comprises a gear pump.

10. The system of claim 2, wherein the processor is configured to cause the implantable pump to transfer, or cease transfer of, fluid from the peritoneal cavity when the output of the analyte sensor equals or exceeds a predetermined value.

11. The system of claim 2, wherein the processor is configured to cause the implantable pump to transfer, or cease transfer of, fluid from the peritoneal cavity when the output of the analyte sensor equals or falls below a predetermined value.

12. The system of claim 2, wherein the processor is configured to compute an amount of analyte removed from the peritoneal cavity by operation of the implantable pump.

13. The system of claim 2, further comprising a sensor configured to monitor pressure in a bladder, wherein the processor configured to interrupt transfer of fluid by the implantable pump from the peritoneal cavity to the bladder if the pressure in the bladder exceeds a threshold value.

14. The system of claim 2, further comprising a sensor configured to monitor pressure in the peritoneal cavity, wherein the processor further is configured to cease transfer of fluid by the implantable pump from the peritoneal cavity to a bladder if the pressure in the peritoneal cavity falls below a preset limit value.

15. The system of claim 1, wherein the analyte sensor is configured to monitor sodium ion concentration or electrical conductivity.

16. The system of claim 1, wherein the analyte sensor is configured to monitor a concentration of dextrose or icodextrin/dextrin in fluid in the peritoneal cavity.

17. The system of claim 1, wherein the solution further comprises urea or from 0.5 to 50 grams of high molecular weight glucose polymer per 100 ml of aqueous solution or both.

18. The system of claim 1, wherein the processor is configured to estimate an amount of sodium transferred from the peritoneal cavity using the output of the analyte sensor.

19. A system for use with a direct sodium removal (DSR) solution for conducting direct sodium removal therapy in a patient, the system comprising:

an infusate configured to be introduced into a peritoneal cavity, the infusate being a solution with a sodium content less than 35 meq/L and consisting of 0.5 to 50 grams dextrose per 100 ml of aqueous solution, 0.5 to 50 grams icodextrin/dextrin per 100 ml of aqueous solution, and purified water;

an analyte sensor configured to output a signal indicative of an analyte concentration associated with the infusate introduced into the peritoneal cavity; and a processor coupled to the analyte sensor and configured to receive the signal indicative of the analyte concentration.

20. A method of performing direct sodium removal (DSR) therapy to remove excess sodium from a patient to reduce fluid overload, the method comprising:

introducing an infusate into a peritoneal cavity, the infusate comprising a solution having a sodium content less than 35 meq/L and (i) from 0.5 to 50 grams dextrose per 100 ml of aqueous solution, (ii) from 0.5 to 50 grams icodextrin/dextrin per 100 ml of aqueous solution, and (iii) purified water;

monitoring analyte concentration associated with the infusate introduced into the peritoneal cavity using an analyte sensor; and receiving an output from the analyte sensor indicative of the analyte concentration.

21. The method of claim 20, further comprising pumping fluid from the peritoneal cavity responsive either to the output of the analyte sensor or after expiration of a predetermined dwell time.

* * * * *